US011678918B2

(12) United States Patent
Hale

(10) Patent No.: US 11,678,918 B2
(45) Date of Patent: Jun. 20, 2023

(54) APPARATUS AND METHOD FOR A TRANSALVEOLAR DENTAL IMPLANT

(71) Applicant: Individual Implant Solutions, Inc., Woodland Hills, CA (US)

(72) Inventor: Robert G. Hale, Woodland Hills, CA (US)

(73) Assignee: Individual Implant Solutions, Inc., Woodland Hills, CA (US)

( * ) Notice: Subject to any disclaimer, the term of this patent is extended or adjusted under 35 U.S.C. 154(b) by 426 days.

(21) Appl. No.: 16/866,957

(22) Filed: May 5, 2020

(65) Prior Publication Data
US 2020/0261131 A1  Aug. 20, 2020

Related U.S. Application Data

(63) Continuation of application No. 16/030,276, filed on Jul. 9, 2018, now Pat. No. 10,702,319.

(51) Int. Cl.
*A61B 17/80* (2006.01)
*A61C 8/00* (2006.01)
(Continued)

(52) U.S. Cl.
CPC ........ *A61B 17/8071* (2013.01); *A61C 8/0012* (2013.01); *A61C 8/0034* (2013.01);
(Continued)

(58) Field of Classification Search
CPC . A61C 8/0012; A61C 8/0034; A61B 17/8071; B33Y 10/10; B33Y 80/00; B22F 2301/205
See application file for complete search history.

(56) References Cited

U.S. PATENT DOCUMENTS 4,253,833 A    3/1981  Edelman
4,553,939 A    11/1985 Roberts
(Continued)

FOREIGN PATENT DOCUMENTS

DE    10 2015 122 800 B3    5/2017
EP         3 017 785 A1    5/2016
(Continued)

OTHER PUBLICATIONS

Extended European Search Report dated Feb. 17, 2022 in European Patent Application No. 19833818.8, 11 pages.
(Continued)

*Primary Examiner* — Nicholas D Lucchesi
(74) *Attorney, Agent, or Firm* — Oblon, McClelland, Maier & Neustadt, L.L.P.

(57) ABSTRACT

The present disclosure relates to single tooth or full arch dental restoration. In cases where patients have insufficient bone stock for conventional root-form dental implants, current solutions often fail to restore function. The present disclosure describes a transalveolar dental implant for single tooth or full arch dental restoration. The transalveolar dental implant is comprised of a post and a bone plate, the bone plate having a contoured portion fabricated to match the topography of a bony surface of the facial skeleton. Through primary fixation of the contoured portion of the bone plate, the transalveolar dental implant improves function and outcomes in affected patients.

8 Claims, 16 Drawing Sheets

(51) Int. Cl.
    *B33Y 80/00*        (2015.01)
    *B22F 10/28*        (2021.01)
    *B33Y 10/00*        (2015.01)

(52) U.S. Cl.
    CPC .............. *B22F 10/28* (2021.01); *B33Y 80/00* (2014.12); *B22F 2301/205* (2013.01); *B33Y 10/00* (2014.12)

(56) References Cited

U.S. PATENT DOCUMENTS

| | | | |
|---|---|---|---|
| 4,702,697 A | 10/1987 | Linkow | |
| 5,052,930 A | 10/1991 | Lodde | |
| 5,116,226 A | 5/1992 | Linkow | |
| 5,201,736 A | 4/1993 | Strauss | |
| 5,769,637 A | 6/1998 | Morgan | |
| 5,873,721 A | 2/1999 | Willoughby | |
| 6,599,516 B1 | 7/2003 | Knaack | |
| 8,282,635 B1 | 10/2012 | Amato | |
| 2007/0055254 A1 | 3/2007 | Ihde | |
| 2008/0248441 A1 | 10/2008 | De Clerck | |
| 2010/0003638 A1* | 1/2010 | Collins | A61K 6/818 433/174 |
| 2011/0008755 A1 | 1/2011 | Misch | |
| 2011/0166572 A1 | 7/2011 | Ihde | |
| 2011/0236858 A1 | 9/2011 | Delmonico | |
| 2012/0028213 A1 | 2/2012 | Meitner | |
| 2013/0065191 A1 | 3/2013 | Carrillo Fuentevilla | |
| 2014/0080091 A1 | 3/2014 | Chan et al. | |
| 2014/0324046 A1 | 10/2014 | Vicatos | |
| 2014/0349251 A1 | 11/2014 | Moon | |
| 2015/0147720 A1* | 5/2015 | Lai | A61C 8/0013 433/173 |
| 2016/0120582 A1 | 5/2016 | Martinez Navarro | |
| 2017/0000497 A1 | 1/2017 | Wolfe et al. | |
| 2017/0238984 A1 | 8/2017 | Kleiner | |
| 2017/0348023 A1 | 12/2017 | Thiel | |
| 2018/0132870 A1 | 5/2018 | De Clerck | |
| 2020/0261189 A1 | 8/2020 | Waizenegger et al. | |

FOREIGN PATENT DOCUMENTS

| | | |
|---|---|---|
| WO | WO 2016/181286 A1 | 11/2016 |
| WO | 2017/161121 A1 | 9/2017 |
| WO | WO 2018/041574 A1 | 3/2018 |

OTHER PUBLICATIONS

International Search Report and Written Opinion dated Oct. 29. 2019 for International Application No. PCT/US2019/041049, 19 pgs.
Combined Chinese Office Action and Search Report dated Jan. 7, 2022 in corresponding Chinese Patent Application No. 201980058446.0 (with English Translation), 22 pages.

* cited by examiner

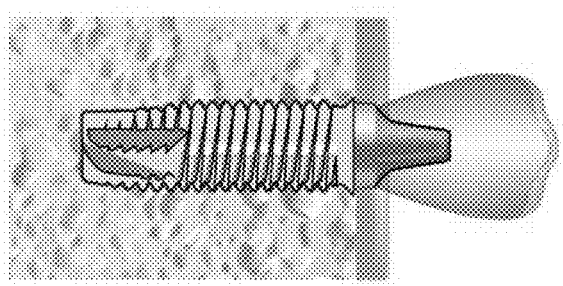
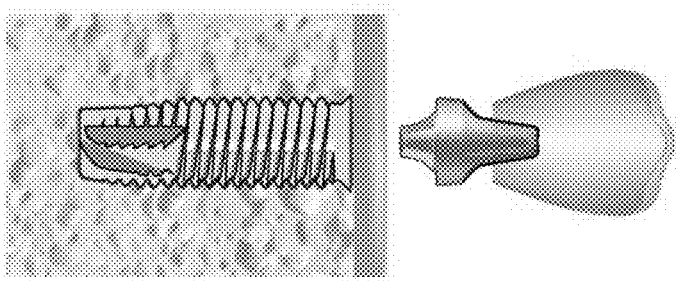
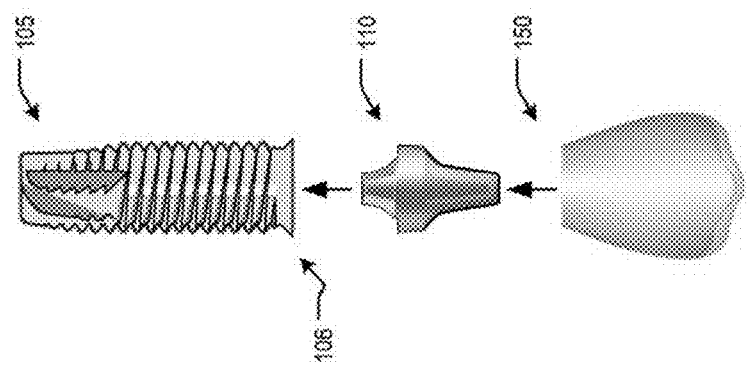
FIG. 1A (Prior Art)

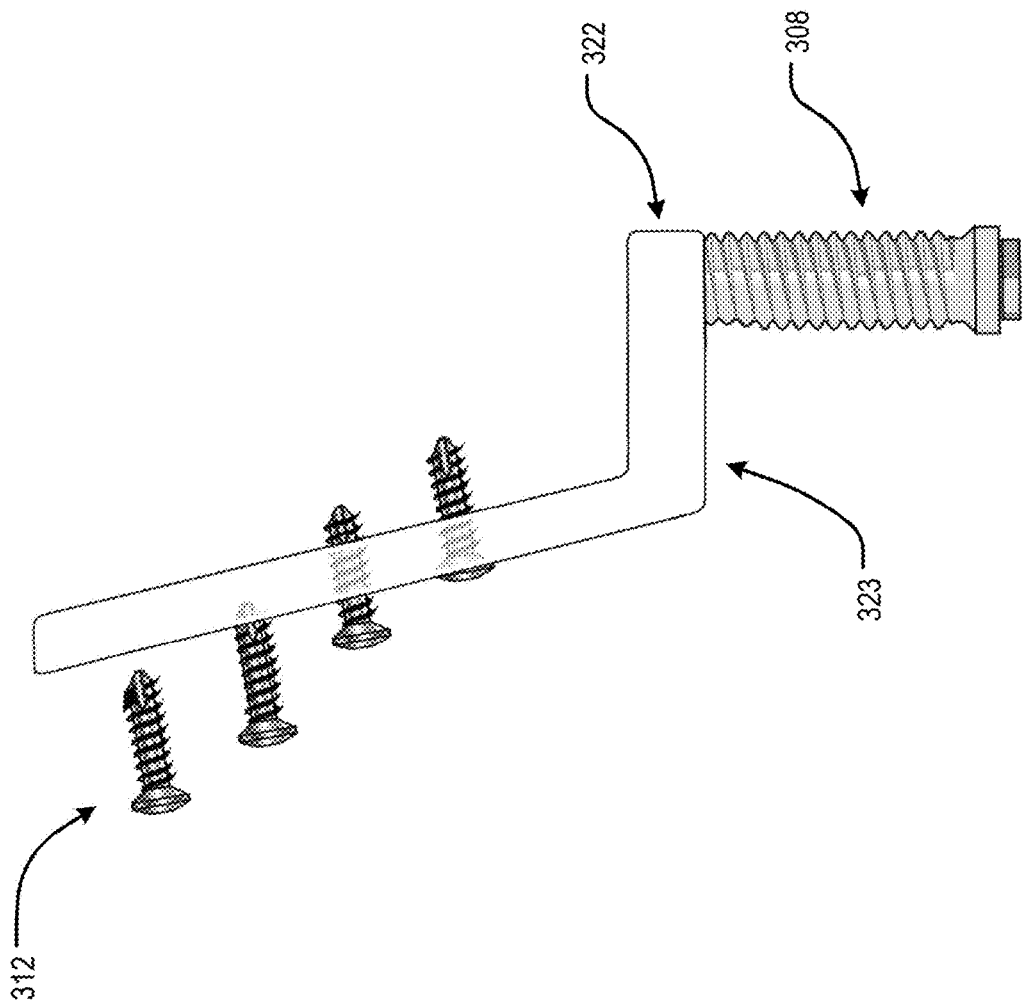
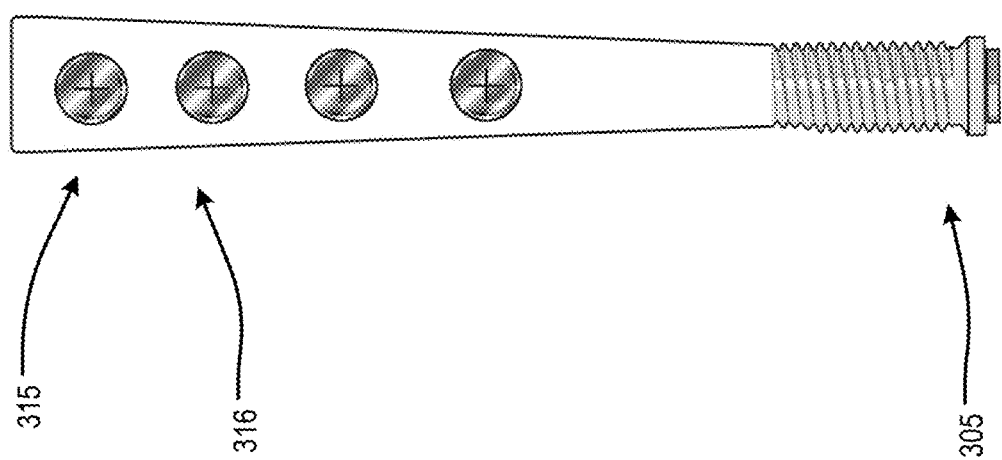

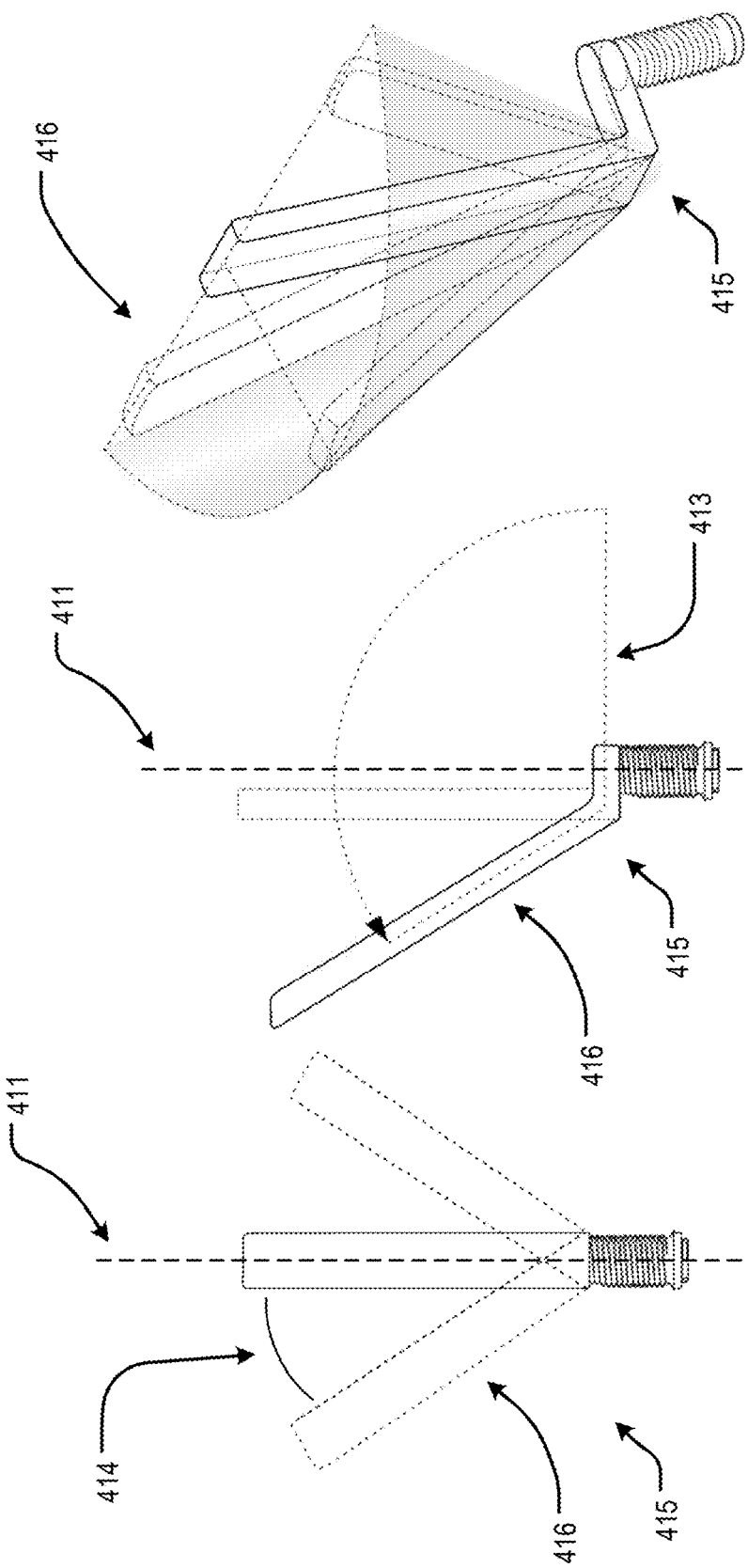

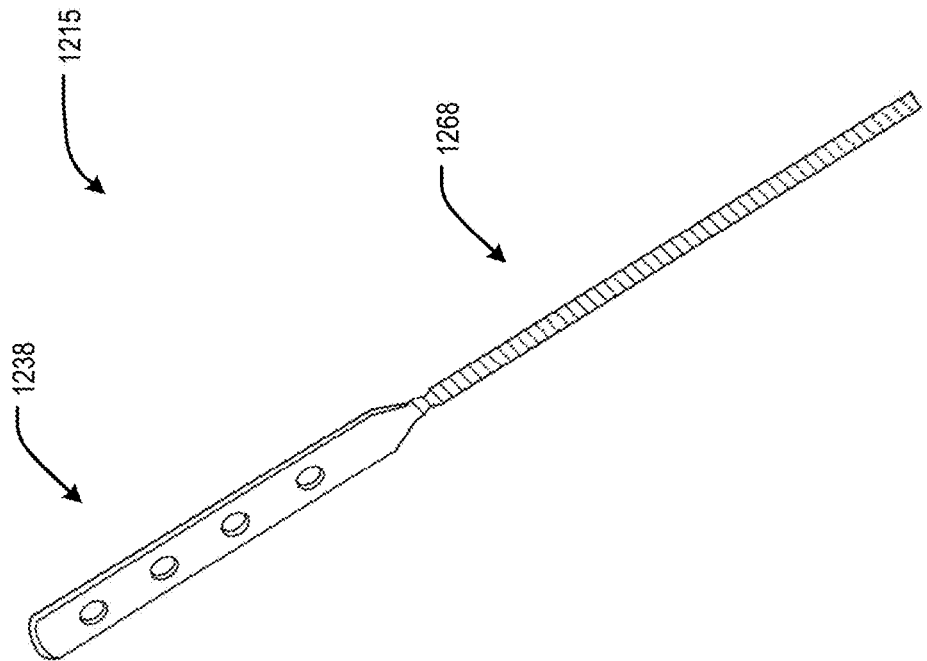
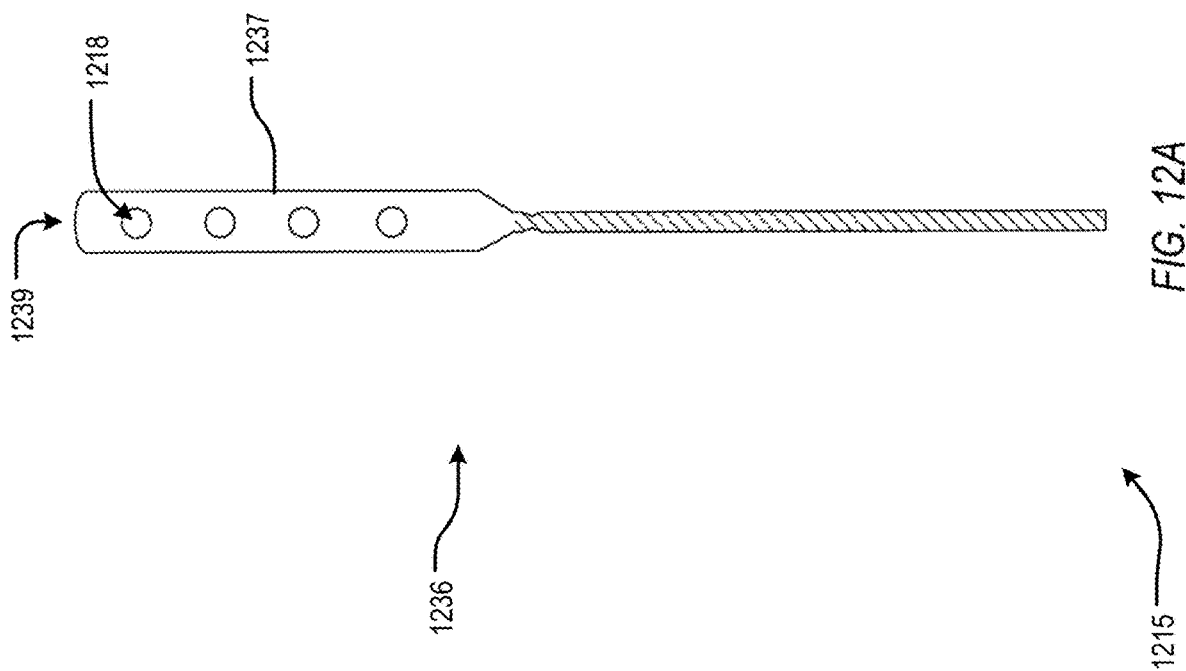
FIG. 12B
FIG. 12A

APPARATUS AND METHOD FOR A TRANSALVEOLAR DENTAL IMPLANT

CROSS-REFERENCE TO RELATED APPLICATIONS

The present application is a continuation of U.S. patent application Ser. No. 16/030,276, filed Jul. 9, 2018, which is incorporated by reference herein in its entirety for all purposes.

BACKGROUND FIELD OF THE DISCLOSURE

The present disclosure relates to the field of oral and maxillofacial surgery and, specifically, dental implant surgery for the restoration of dentition.

DESCRIPTION OF THE RELATED ART

Partial edentulism, or in severe cases, complete edentulism, the loss of all teeth, can have serious repercussions on mastication, speech, and aesthetics. Dental implant surgery, an alternative to dentures or bridgework, replaces tooth roots with metal posts and damaged or missing teeth with artificial teeth that are functionally and aesthetically similar to native teeth. Like native teeth, these artificial teeth are secured in the alveolar bone via a post, or screw-like component, which provides rigid fixation through osseointegration and, additionally, distributes load and maintains periprosthetic bone quality.

Typical root-form dental implants, however, require sufficient alveolar bone in order to promote osseointegration and allow proper load bearing and function. In cases of insufficient alveolar bone, as a result of severe bone loss or skeletal pre-disposition, alternative strategies, often time-intensive with variable success rates, must be employed. A robust approach to dental reconstruction has yet to be developed.

The foregoing "Background" description is for the purpose of generally presenting the context of the disclosure. Work of the inventors, to the extent it is described in this background section, as well as aspects of the description which may not otherwise qualify as prior art at the time of filing, are neither expressly or impliedly admitted as prior art against the present invention.

SUMMARY

According to an embodiment, the present disclosure relates to a dental implant, comprising a bone plate having a planar portion and a contoured portion, and a post, wherein the planar portion of the bone plate and the post are positioned within a vertical slot osteotomy, wherein one or more surfaces of the contoured portion of the bone plate is contoured relative to a selected surface of a bone of a facial skeleton, and wherein the bone plate is configured to be coupled to the facial skeleton.

According to an embodiment, the present disclosure is further related to a method of manufacture of a dental implant, comprising acquiring, via processing circuitry, structural data corresponding to a facial skeleton, selecting, via the processing circuitry, a surface of a bone of the facial skeleton based upon a determination of cortical bone thickness, generating, via the processing circuitry, a contoured surface based upon the selection of the surface of the bone of the facial skeleton, and fabricating, based upon an instruction transmitted via the processing circuitry, a bone plate based upon the generated contoured surface, wherein the bone plate comprises a planar portion and a contoured portion, the planar portion of the bone plate being positioned within a vertical slot osteotomy and the contoured portion being positioned proximately to the selected surface of the bone of the facial skeleton, and wherein the bone plate is configured to be coupled to the facial skeleton.

According to an embodiment, the present disclosure is further related to a dental implant, comprising a bone plate having one or more surfaces contoured relative to a selected surface of a bone of a facial skeleton, and a projecting portion, the projecting portion of the dental implant extending from and below the bone plate, wherein the projecting portion is configured to be coupled to a dental prosthesis, and wherein the bone plate is configured to be coupled to the facial skeleton.

The foregoing paragraphs have been provided by way of general introduction and are not intended to limit the scope of the following claims. The described embodiments, together with further advantages, will be best understood by reference to the following detailed description taken in conjunction with the accompanying drawings.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein:

FIG. 1A is a schematic of a dental implant system;

FIG. 3A is a schematic of an anterior view of a transalveolar dental implant, according to an exemplary embodiment of the present disclosure;

FIG. 3B is a schematic of a lateral view of a transalveolar dental implant, according to an exemplary embodiment of the present disclosure;

FIG. 4A is a schematic of an anterior view of a transalveolar dental implant, according to an exemplary embodiment of the present disclosure;

FIG. 4B is a schematic of a lateral view of a transalveolar dental implant, according to an exemplary embodiment of the present disclosure;

FIG. 4C is a perspective view of a transalveolar dental implant, according to an exemplary embodiment of the present disclosure;

FIG. 12A is a schematic of an anterior view of a transvestibular dental implant, according to an exemplary embodiment of the present disclosure;

FIG. 12B is a schematic of a perspective view of a transvestibular dental implant, according to an exemplary embodiment of the present disclosure;

DETAILED DESCRIPTION

The terms "a" or "an", as used herein, are defined as one or more than one. The term "plurality", as used herein, is defined as two or more than two. The term "another", as used herein, is defined as at least a second or more. The terms "including" and/or "having", as used herein, are defined as comprising (i.e., open language). Reference throughout this document to "one embodiment", "certain embodiments", "an embodiment", "an implementation", "an example" or similar terms means that a particular feature, structure, or characteristic described in connection with the embodiment is included in at least one embodiment of the present disclosure. Thus, the appearances of such phrases or in various places throughout this specification are not necessarily all referring to the same embodiment. Furthermore, the particular features, structures, or characteristics may be combined in any suitable manner in one or more embodiments without limitation.

Figure 1B:
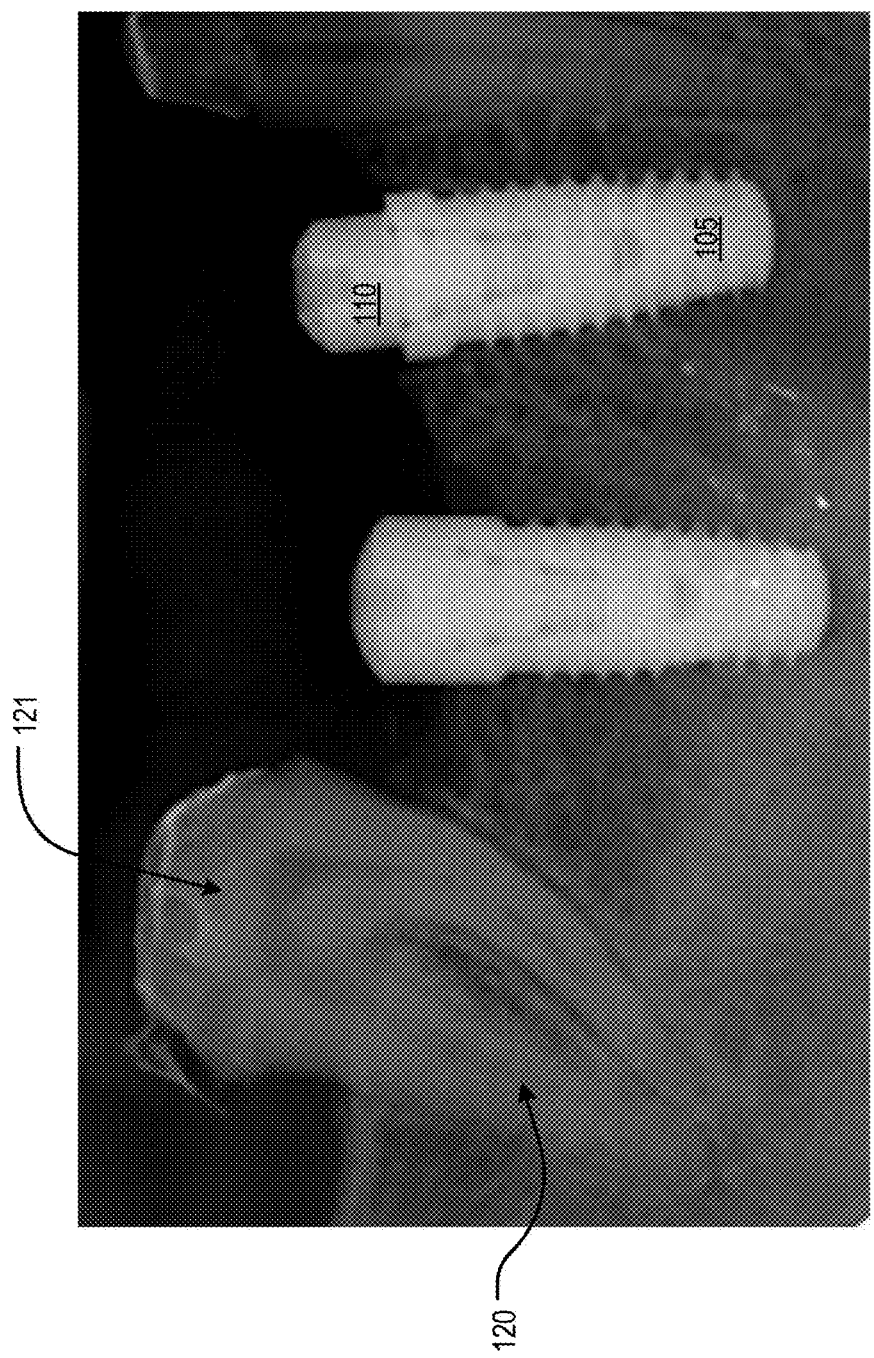
FIG. 1B is a radiograph of a dental implant system in vivo.

Root-form dental implants, as seen in FIG. 1A, are an effective strategy for dental reconstruction when sufficient alveolar bone is present. Compared with tooth-supported dental bridges, root-form dental implants, fixed within the alveolar bone, are able to maintain the health of the underlying bone by preserving bone loading. With reference to FIG. 1A, a root-form dental implant is comprised, initially, of a post 105, or screw-like metal component, fixed within the alveolar bone of the facial skeleton. An abutment 110, which serves as a platform for a crown 150 to be added later, is mechanically coupled to a base of the post 106. In a radiograph, as seen in FIG. 1B, the post 105 is rigidly fixed within the alveolar bone, similar to the arrangement of a root 120 of a native tooth 121. In the majority of cases, patients go home with a functional replacement, receive a permanent crown set when the implant is integrated (~4-12 weeks), and are able to return to normal function with improved mastication, speech, and aesthetics.

In cases of inadequate bone, however, as a result of bone atrophy or skeletal pre-disposition, root-form dental implants, as described above, are not a surgical option. In such cases, it may be necessary to resort to special techniques including but not limited to bone grafts directed to bone atrophy, alveolar bone distraction osteogenesis, lifting of the maxillary sinus with bone filling, lateralization of the mandibular bone nerve, corticotomy, and alveolar expansion, with or without graft. While the above approaches offer hope to certain patients, each carries with it a respective set of drawbacks. Generally, these techniques increase chair time and the number of associated laboratory steps required to fit a dental prosthesis. Specifically, as in the case of bone grafting, risks of donor site morbidity and a time-intensive recovery period prior to implantation of dental implant hardware present significant challenges to successful outcomes.

Figure 2:
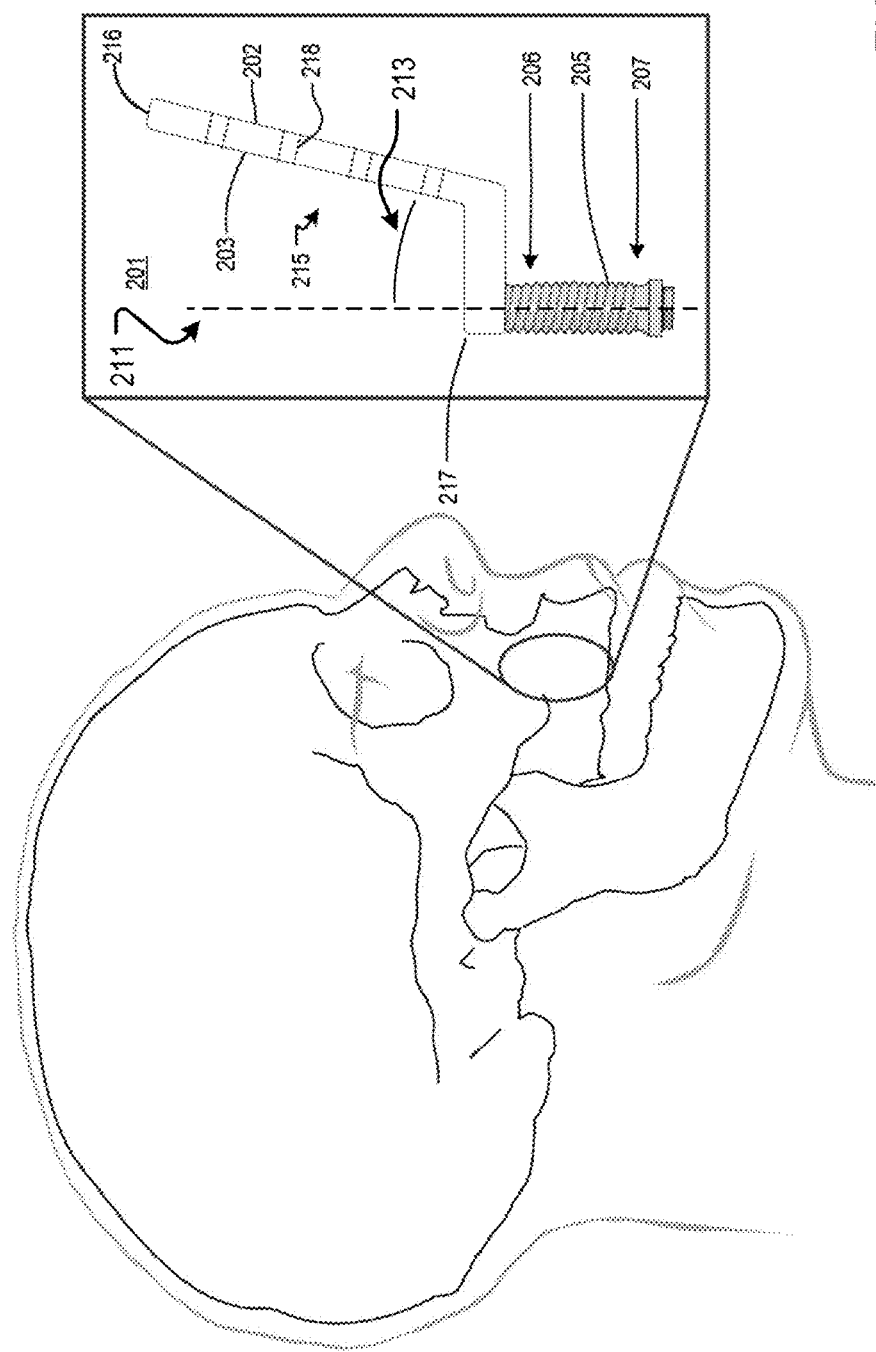
FIG. 2 is a cross-sectional schematic of a transalveolar dental implant, according to an exemplary embodiment of the present disclosure.

To this end, a transalveolar dental implant, as described in the present disclosure and introduced in FIG. 2, improves care for patients with insufficient bone by mitigating the above-described drawbacks associated with alternative strategies while preserving the benefits of root-form dental implants. Briefly, the transalveolar dental implant (TDI) of the present disclosure includes a contoured bone plate extending transalveolarly through an alveolar bone vertical slot osteotomy to an adjacent bone of the facial skeleton, thus providing primary stability to the TDI. The alveolar bone vertical slot osteotomy, with newly resident post, is filled via bone grafting to ensure bone regeneration and stabilization of the post. In an example, where four TDIs are implanted around the dental arch, a full dental arch prosthesis may be coupled to the TDIs for immediate function.

A more detailed description of the present disclosure, including exemplary embodiments, can be found below.

A schematized rendering for descriptive purposes, FIG. 2 describes the TDI 201 of the present disclosure. The TDI 201 is directed to a region of the facial skeleton known as the alveolar bone, a thickened bony region that supports the dental root system. The TDI 201 of the present disclosure includes a post 205. The post 205 includes a post base 207 and a post apex 206. The post base 207 is designed to receive an abutment. The post apex 206, instead of being coupled to trabeculae of the alveolar apex, is coupled to an aspect of the bone plate 215. The bone plate 215 is comprised of two portions. The first portion is a planar portion 217 meant for coupling with the post apex 206 and for physical interaction with a captive surface of an osteotomy, the captive surface being, in an upper arch embodiment of the present disclosure, a superior portion of the osteotomy. The second portion is a contoured portion 216. The contoured portion 216 is contoured with respect to a selected region of the facial skeleton determined to be of sufficient bone quality for fixation. In an embodiment, an axis of the contoured portion 216 may be related to a longitudinal axis 211 of the bone plate 215 by an anterior angle 213. A plurality of through apertures 218 having locking threads and sized in accordance with appropriate screws are disposed along the length of the contoured portion 216 of the bone plate 215, passing from an anterior surface 202 to a posterior surface 203, for fixation of the TDI 201, via the posterior surface 203, to the facial skeleton. In another embodiment, the plurality of through apertures 218, lacking threads and sized in accordance with appropriate screws, may be disposed along the length of the contoured portion 216 of the bone plate 215, passing from the anterior surface 202 to the posterior surface 203, for fixation of the TDI 201, via the poster surface 203, to the facial skeleton.

The quality of bone required for fixation of the contoured portion 216 of the bone plate 215 is related, in part, to the selected screws for fixation and relative to a pre-determined minimum cortical bone thickness. In an example, the pre-determined minimum cortical bone thickness is 1.5 mm. In another example, the pre-determined minimum cortical bone thickness is based upon properties of the selected screw, including but not limited to diameter, pitch, and screw length.

As briefly described, the contoured portion 216 of the TDI 201 is designed in the context of an individual patient's skeletal structure. Following the acquisition and reconstruction of medical images, via a data processing device having a processing circuitry, reflecting the macro- and microstructure of the bone of the facial skeleton, via techniques including but not limited micro-computed tomography, cone beam computed tomography, and high-resolution magnetic resolution imaging, one or more regions of the facial skeleton are selected as receptive to fixation of a bone plate. According to an embodiment, and as mentioned above, this determination is made based upon local cortical bone thickness, wherein sufficient cortical bone, the dense outer surface of bone, is required to prevent fracture during bone plate fixation. Following region selection, a reconstructed model of the one or more regions of interest is then further manipulated via software (e.g. Mimics, SolidWorks) and prepared for manufacturing, as would be understood by one of ordinary skill in the art. According to an embodiment, the posterior surface 203 of the bone plate 215 is contoured relative to the selected facial skeleton region and the anterior surface 202 of the bone plate 215 is substantially planar. It should be appreciated that the anterior surface 202 of the bone plate 215 may be of a variety of contours, in a nonlimiting manner, such that rigid fixation, via screws through the plurality of through apertures 218, may be realized.

Each bone plate 215 is manufactured in order to allow rigid fixation to the facial skeleton of the patient and to promote osseointegration between the TDI 201 and the periprosthetic bone. To this end, and according to an embodiment, the TDI 201 of the present disclosure can be manufactured from one of a group of materials including but not limited to titanium, cobalt-chrome, cobalt-chrome-molybdenum, cobalt-chrome-nickel, cobalt-nickel-chrome-molybdenum-titanium, calcium phosphate-derivative coated metals, zirconia, zirconium-coated metals, titanium-coated metals, and other biocompatible metals. In an example, the material selected for each component of the TDI 201 is similar. Further, and according to an embodiment, the TDI 201 of the present disclosure can be manufactured via a variety of additive manufacturing or subtractive manufacturing techniques including but not limited to direct metal laser sintering, injection molding, iterative plate bending and computer-aided manufacturing. In another embodiment, the bone plate 215 and the post 205 are manufactured separately, the bone plate 215 being fabricated according to the above-described techniques and the post 205 being manufactured according to techniques understood by one of ordinary skill in the art. In another embodiment, the bone plate 215 and the post 205 are manufactured together via three-dimensional metal printing. Following fabrication, the two components of the TDI 201 can be coupled at a junction consisting of the planar portion 217 of the bone plate 215 and the post apex 206 of the post 205. The coupling can be formed by a variety of approaches including but not limited to welding, frictional coupling, and structural adhesives. In the context of the present disclosure, screws are selected for the plurality of through apertures 218, or may be fabricated according to pre-determined specifications, in order to ensure rigid fixation of the bone plate 215 to the facial skeleton.

Further, and according to an embodiment, the TDI 201 of the present disclosure is manufactured according to physical dimensions of the selected skeletal features of each patient. As described above, the contoured portion 216 of the bone plate 215 is manufactured according to the selected skeletal region of each patient, the dimensions of the contoured portion 216 dependent, thereof. The number of through apertures 218, likewise, is dependent on the selected skeletal region and the minimum number of screws required in order to secure the bone plate 215 to the facial skeleton. In an embodiment, the post 205 and the planar portion 217 of the bone plate 215 can be selected from a group of pre-determined sizes, their dimensions determined therein. In another embodiment, the post 216 and the planar portion 217 of the bone plate 215 may be custom manufactured according to the needs of the patient, the dimensions of the planar portion 217 of the bone plate 215 and post 216 being dependent, thereof. It should be appreciated that, using the above-described techniques and approaches, the present disclosure affords the flexibility to fabricate the TDI 201 with necessary dimensions based upon the needs of the individual patient.

According to an embodiment, a width of the bone plate 215 is equal to the diameter of the post 205. The thickness of the bone plate 215 is determined according to the length of the bone plate 215, wherein a longer bone plate 215 requires an increase in thickness of the bone plate 215 to support the post 205 and prevent excess micromotion. In an example, the thickness of the bone plate 215 ranges between 1.00 mm and 3.00 mm, and preferably between 1.25 mm and 2.00 mm. The length of the bone plate 215, therefore, is determined according to locally sufficient cortical bone.

According to an embodiment, the relative position of the post 205 and the contoured portion 216 of the bone plate 215 along a bone plate axis, defined as an axis including the longitudinal axis 211 of the bone plate 215, should be such that sufficient mechanical structure is provided to the TDI to withstand vertical loading. In an example, the anterior angle 213 between the post 205 and the contoured portion 216 of the bone plate 215 along the plate axis ranges between 90° and 180°, and preferably between 135° and 180°.

According to an embodiment, and in accordance with United States Food and Drug Administration Class 2 Special Controls Guidance on Root-form Endosseous Dental Implants and Endosseous Dental Abutments, the diameter of the post 205 may be no smaller than 3.25 mm, the length of the post no smaller than 7.00 mm, and the abutment offset by no more than 30° from a longitudinal axis of the post.

To this end, FIG. 3A and FIG. 3B are exemplary embodiments of the TDI of the present disclosure. As shown in FIG. 3A, an anterior view, the TDI may comprise a bone plate 315 having a contoured portion 316, specific to selected skeletal features, and a post 305. As shown in FIG. 3B, a lateral view, the TDI may further comprise a plurality of screws 312 configured according to a dimension of a corresponding plurality of through apertures. In an embodiment, a thickness of the planar portion of the bone plate 322 may be between 1.00 mm and 2.00 mm and a length of the planar portion of the bone plate 323 may be between 3.00 mm and 5.00 mm. In an example, the thickness of the planar portion of the bone plate 322 may be 2.00 mm and a length of the planar portion of the bone plate 323 may be 4.00 mm. In another embodiment, as alluded to above, a length of a post 308 may be between 7.00 mm and 12.00 mm. In an example, the length of the post 308 may be 8.00 mm.

Moreover, the contoured portion 316 of the bone plate 315 may be angled with respect to the post 305. FIG. 4A, FIG.

4B, and FIG. 4C are illustrations of a variety of angular configurations of the contoured portion of the bone plate. In an embodiment, as shown in FIG. 4A, a lateral angle 414 of a contoured portion 416 of a bone plate 415 may be between −60° and +60° relative to a longitudinal axis 411 of the bone plate 415, in a first plane. In another embodiment, the lateral angle 414 of the contoured portion 416 of the bone plate 415 may be between −45° and +45°. In an example, the lateral angle 414 of the contoured portion 416 of the bone plate 415 may be +25°. In another embodiment, as shown in FIG. 4B, an anterior angle 413 of the contoured portion 416 of the bone plate 415 may be between −60° and +60° relative to the longitudinal axis 411 of the bone plate 415, in a second plane. In another embodiment, the anterior angle 413 of the contoured portion 416 of the bone plate 415 may be between −45° and +45°. In an example, the anterior angle 413 of the contoured portion 416 of the bone plate 415 may be +15°. FIG. 4C is a schematic of a perspective view of the TDI of the present disclosure, wherein a range of positions of the contoured portion 416 of the bone plate 415 may be visualized. In an embodiment, a variety of anterior angles 413 and lateral angles 414 may be concurrently realized.

According to an embodiment, the above described ranges of anterior angles 413 and lateral angles 414 are determined such that the bone plate 415 may withstand normal loading forces during movement of the mouth including mastication, wherein anterior angles 413 and lateral angles 414 approximating 0° (or 180° in a different orientation) are ideal for load transfer.

Figure 5:
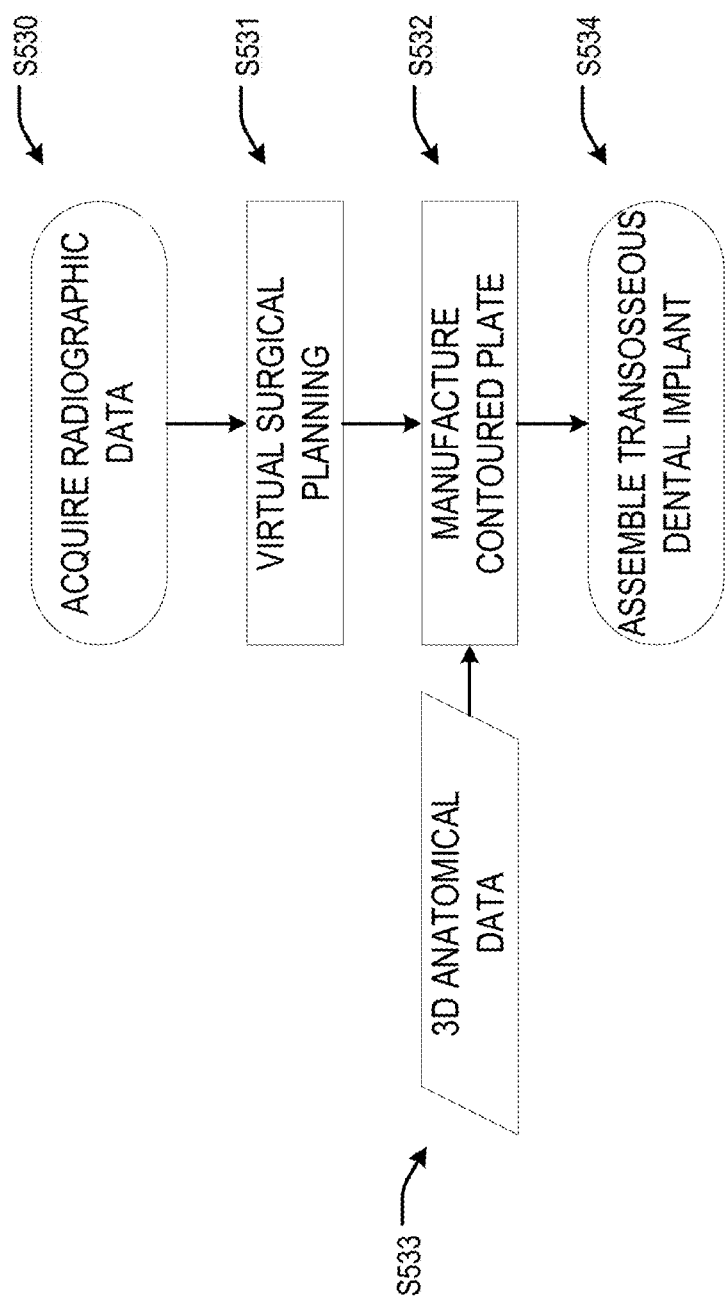
FIG. 5 is a flowchart of fabrication of a transalveolar dental implant, according to an exemplary embodiment of the present disclosure.

Manufacture of the TDI, according to an exemplary embodiment, is described in the flowchart of FIG. 5. First, a cone beam computed tomography (CBCT or C-arm CT) of the facial skeleton (e.g., maxilla, mandible) is performed S530. The CBCT is aided by the use of radiopaque stents that provide a preview of a final restoration relative to adjacent structures, allowing for informed surgical planning. The radiopaque stent(s) also position the jaws into centric relation with proper vertical dimension of occlusion. Next, virtual surgical planning, performed via the data processing device, locates TDI positions S531 with alignment of a custom contoured bone plate along sufficiently thick cortical bones of the adjacent facial skeleton. According to an embodiment, the adjacent facial skeleton includes but is not limited to the nasomaxillary pillars and the zygomatic buttresses. Following selection of the regions of interest, and after incorporating three-dimensional anatomical data into software S533, via the data processing device, the planar portion and contoured portion of the bone plate may be manufactured S532 according to the above-described methods. In an example, the bone plate is manufactured via additive titanium laser sintering to promote osseointegration. During assembly S534, the post apex is welded to a surface of the planar portion of the bone plate such that a longitudinal axis of the post is perpendicular to the surface of the planar portion of the bone plate. The post, which extends from the post apex and protrudes through the mid crest of the alveolar bone, is manufactured according to the above-described methods in order to accept dental implant abutments. Both the bone plate and associated screws provide locking technology to prevent loosening during loading. In addition to the TDI, polyethylene templates, drill guides, and drill stop bushings can be manufactured via computer-aided design/computer-aided machining techniques to guide osteotomies. For example, the above-described polyethylene templates, drill guides, and drill stop bushings may be custom manufactured such that the angle, diameter, and depth of an osteotomy is controlled according to the skeletal structure of an individual patient. In an example, osteotomies are performed via side- and end-cutting surgical burs.

According to an embodiment, selection of the regions of interest during the manufacture of the TDI may be performed by the processing circuitry according to a skeletal parameter, for example, a minimal thickness of cortical bone. In another embodiment, selection of the regions of the interest during the manufacture of the TDI may be performed by a surgeon.

The shape of the above described TDI, as manufactured in FIG. 5 and with reference again to FIG. 2, allows for rigid fixation of the TDI to the facial skeleton and positions the post proximately to a region of the alveolar bone such that an abutment, and subsequent crown, may be coupled in proper position for normal dental function. In order to achieve this, and according to an embodiment of the present disclosure, implantation follows the flowchart described in FIG. 6.

Figure 6:
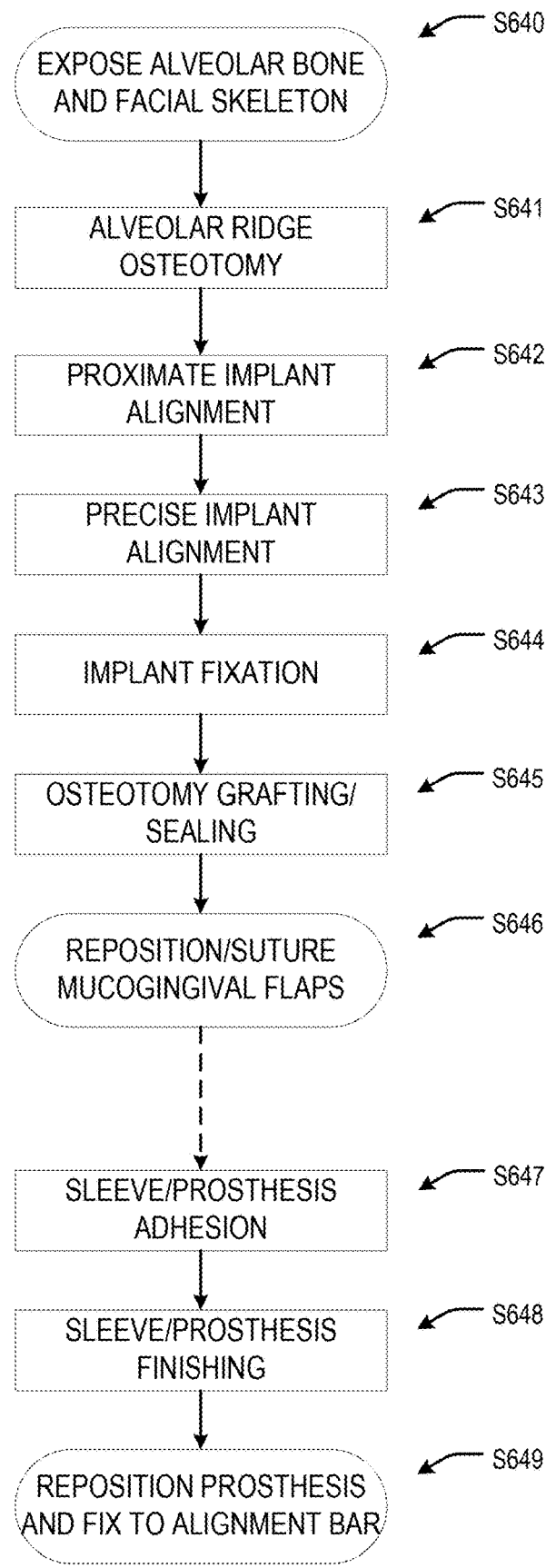
FIG. 6 is a flowchart of implantation of a transalveolar dental implant, according to an exemplary embodiment of the present disclosure.

FIG. 6 describes a method of full arch dental restoration. It should be appreciated that, while FIG. 6 describes implantation of a plurality of TDIs and restoration of a full dental arch (e.g. upper or lower), according to an embodiment of the present disclosure, implantation of a single TDI can be performed similarly mutatis mutandis.

Initially, as described in FIG. 6 and according to an embodiment of the present disclosure, the alveolar bone and facial skeleton are exposed following mid-crestal, full arch gingival incisions and reflection of mucogingival flaps S640. Following preparation of the alveolar ridge, four vertical slot osteotomies are completed with corresponding template guides S641. Each of the four TDIs are positioned into their respective vertical osteotomy slots and positioned proximately with the cortical bones of the facial skeleton S642. Next, a dental arch-shaped titanium alignment bar is placed over the post base of the TDIs and secured to the post via abutment screws, giving the TDIs a final alignment to the facial skeleton S643. Locking self-drilling screws can then be secured through the plurality of through apertures of the contoured portion of the bone plate to fix the TDIs in a precisely aligned position S644 on the facial skeleton. The vertical slot osteotomies are grafted with cortical bone particles produced therefrom, embedding the post of the TDI. A collagen, or other acceptable membrane, is subsequently placed over the grafted sites to confine the cortical bone particles and enhance bone regeneration S645. Lastly, the mucogingival flaps are repositioned over the bone and circumferentially around the post, and sutured S646 to seal the oral environment from the bone/implant interface while keeping the post base exposed for further modification.

In an embodiment of full arch dental restoration, and due to load sharing and cross-arch stability, the alignment bar is further outfitted with a prosthesis immediately following TDI implantation. According to an exemplary embodiment, following repositioning of the mucogingival flaps, a titanium sleeve is positioned over the alignment arch bar and a pre-fabricated (i.e., polymethylmethacrylate) milled prosthesis, with a palate breakout feature, is attached to the alignment arch bar and sleeve. The sleeve is then attached to the prosthesis with common dental adhesive technologies. In an embodiment, and in order to prevent the dental adhesives from contacting the wound environment directly, a soft tissue barrier is included. Next, the prosthesis and connected sleeve are removed and voids between the sleeve and the underside of the prosthesis are filled with dental materials and finished until smooth S648. In completion, the finished prosthesis is then fixed to the alignment bar with mechanical devices or adhesives.

According to another embodiment, wherein one or more individual TDIs are implanted instead of a full arch, the stability of each TDI is evaluated post-operatively to determine the strength of implant fixation and whether or not immediate loading is possible. In evaluating implant stability, one of a variety of methods for determining an ISQ, or Implant Stability Quotient (Osstell), may be employed. In the event the ISQ of an individual TDI is below a minimum for adequate implant fixation, a recovery period of 4 to 12 weeks may be required.

In another embodiment of the present disclosure, and following, in part, the flowchart of FIG. 6, the above-described transalveolar dental implant may be employed in situations of previously failed endosseous dental implants, mutatis mutandis. In an exemplary embodiment, one or more endosseous dental implants, supporting a full arch dental prosthesis, are in a failed state. Following identification of the implant size and implant type via radiographic implant matching, virtual surgical planning and computer-aided design/computer-aided manufacturing are used to design and manufacture an appropriate TDI replacement, referred to herein as a "rescue" TDI (rTDI). Similar to the flowchart of FIG. 6, following exposure of the surgical site via reflection of the mucogingival flaps, the failed one or more endosseous dental implants are bone removed and debrided. One or more vertical slot osteotomies are performed in the alveolar ridge via templates, including bushings, to provide a pathway for each rTDI to be proximately located in the correct dental arch position. A precisely aligned rTDI is realized via engagement of a post of the rTDI with original hardware of the prosthetic device. Similar to the alignment bar of an above-described embodiment of the present disclosure, upon engagement with the prosthetic device via abutments, each rTDI is fixed to the facial skeleton via a plurality of screws placed through a corresponding plurality of through apertures of the contoured portion of the bone plate. After fixing the implant to the facial skeleton, each of the vertical slot osteotomies is bone grafted and sealed to prevent untoward interaction with the oral environment and to promote osseointegration with the post of each rTDI. The mucogingival flaps can then be repositioned and sutured, leaving the abutments of each post exposed for coupling with the prosthetic device.

According to an embodiment, the above-described bushings and associated polyethylene templates and drill guides may be custom manufactured such that the angle, diameter, and depth of an osteotomy is controlled according to the skeletal structure of an individual patient.

Figure 7:
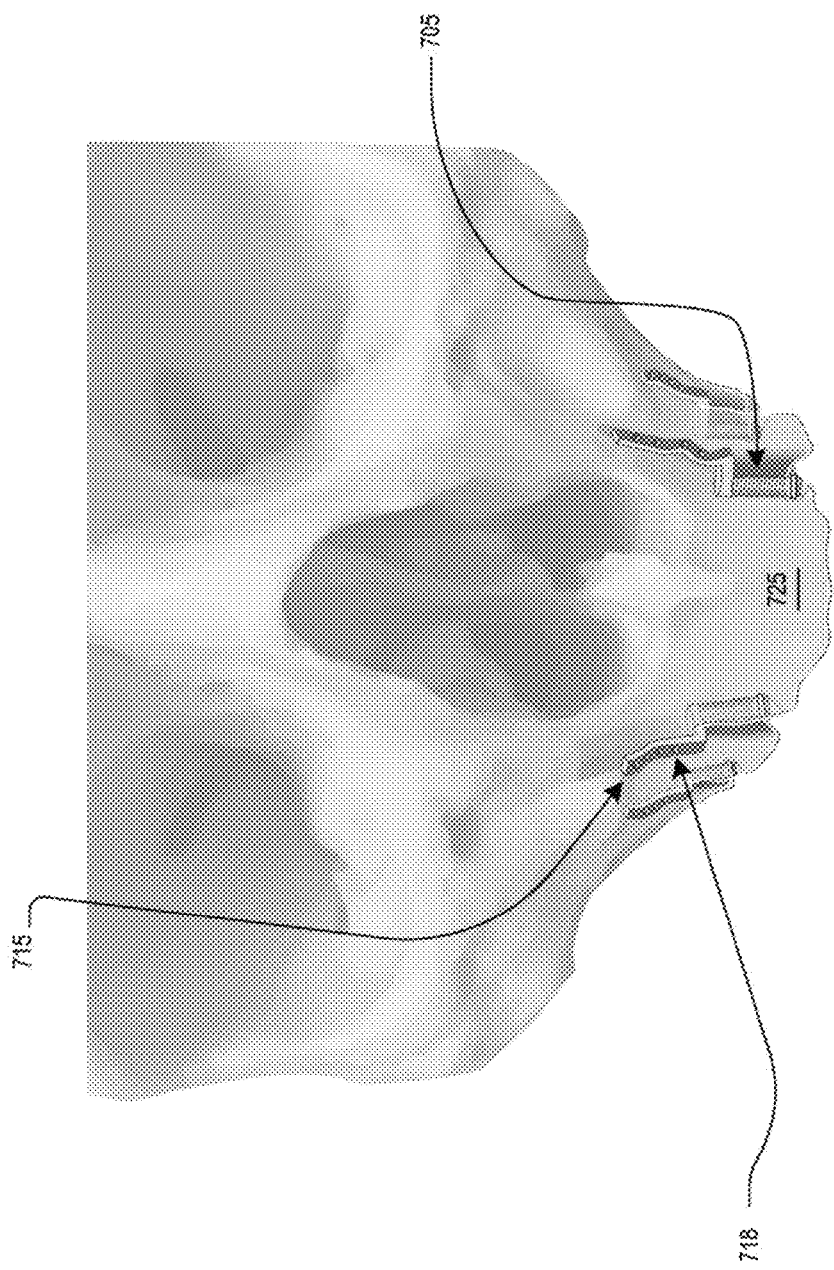
FIG. 7 is an in vitro illustration of one or more implanted transalveolar dental implants from an anterior perspective, according to an exemplary embodiment of the present disclosure.
Figure 8:
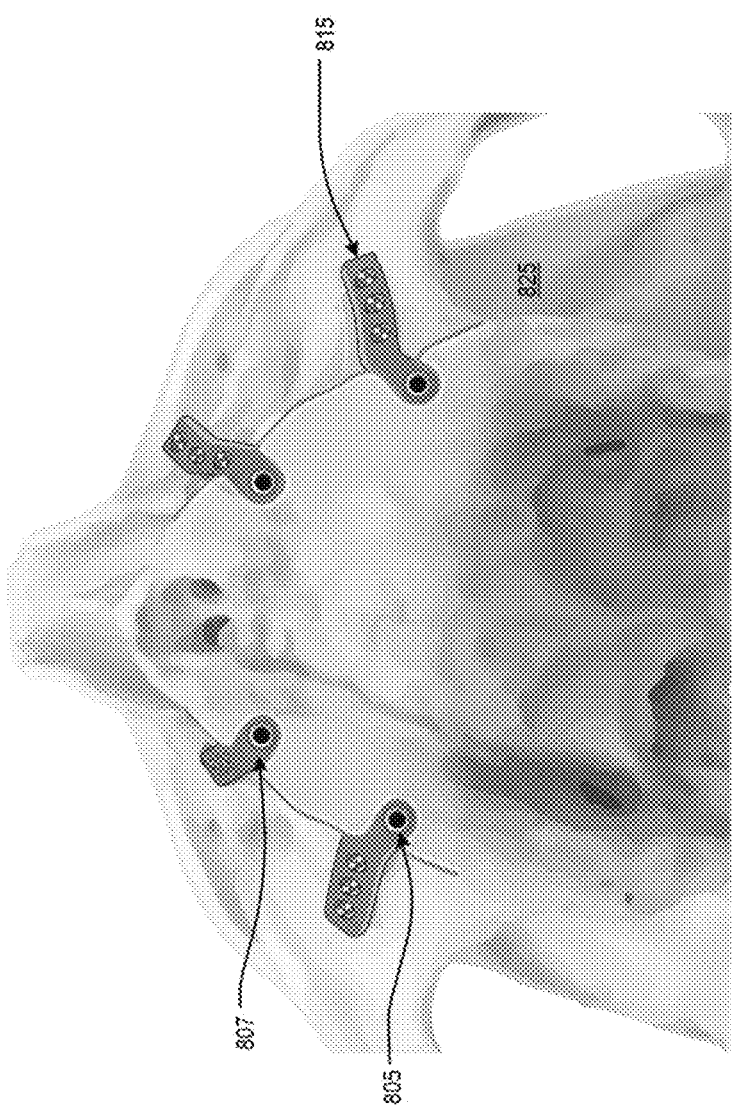
FIG. 8 is an in vitro illustration of one or more implanted transalveolar dental implants from an inferior perspective, according to an exemplary embodiment of the present disclosure
Figure 9:
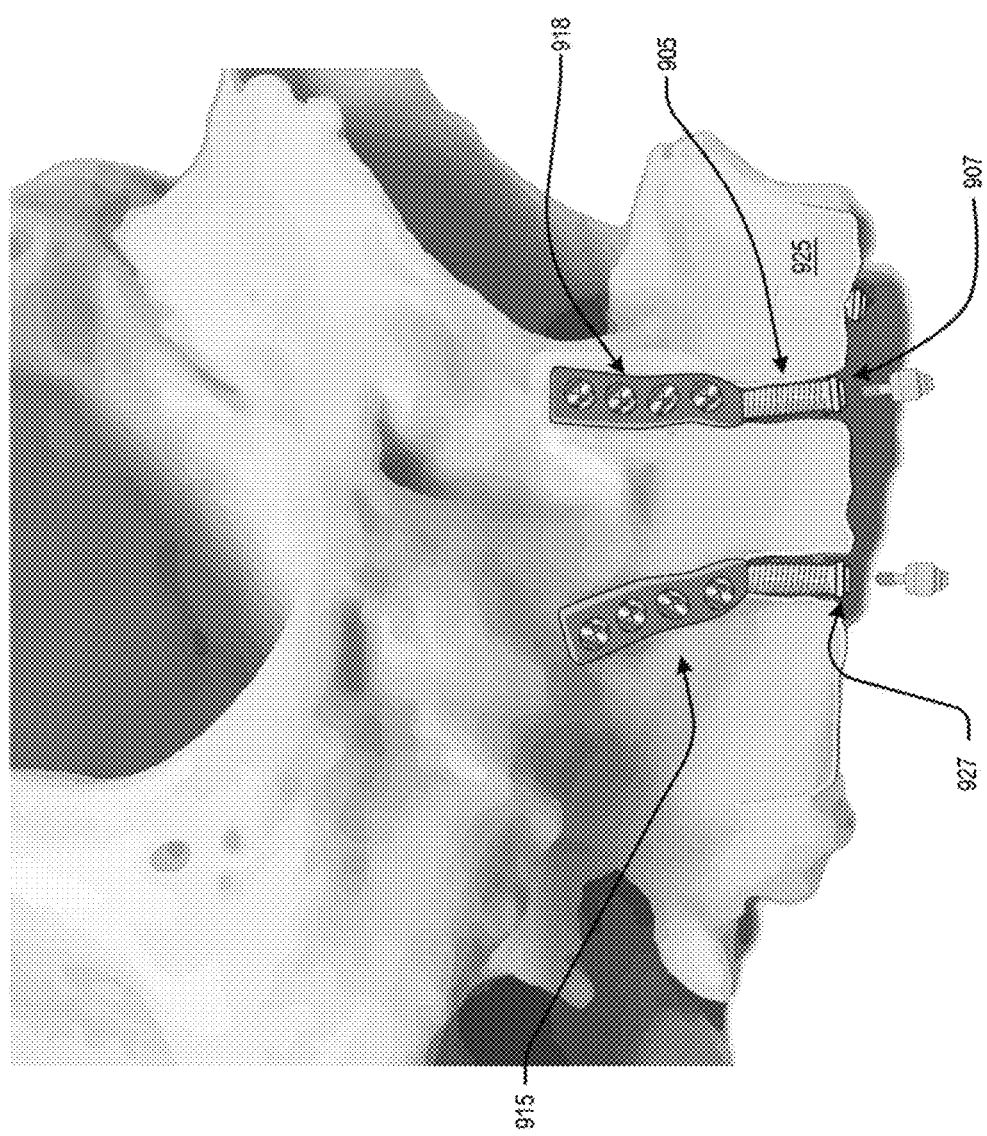
FIG. 9 is an in vitro illustration of one or more implanted transalveolar dental implants from a lateral perspective, according to an exemplary embodiment of the present disclosure.

An in vitro demonstration of components of the full arch restoration presented in FIG. 6 is illustrated in FIG. 7, FIG. 8, and FIG. 9.

FIG. 7 is an in vitro illustration of one or more implanted TDIs from an anterior perspective, according to an exemplary embodiment of the present disclosure. For each of the one or more implanted TDIs, a bone plate 715 is secured to the facial skeleton via screws inserted into through apertures 718 of the contoured portion of the bone plate 715. A post 705 is coupled to a planar portion of the bone plate 715, extending through the depth of the vertical slot osteotomy in the alveolar ridge 725.

FIG. 8 is an in vitro illustration of one or more implanted TDIs from an inferior perspective, according to an exemplary embodiment of the present disclosure. For each of the one or more implanted TDIs, a bone plate 815 is secured to the facial skeleton via screws inserted into through apertures of the contoured portion of the bone plate 815. A post 805, with a post base 807, is coupled to a planar portion of the bone plate 815, extending through the depth of the vertical slot osteotomy in the alveolar ridge 825. From the inferior perspective, the approximate relative position of the implanted TDIs within the upper arch is observable. Moreover, the post base 807, the coupling for an abutment, alignment bar, and ultimately, prosthesis, is observable and accessible.

FIG. 9 is an in vitro illustration of one or more implanted TDIs from a lateral perspective, according to an exemplary embodiment of the present disclosure. For each of the one or more implanted TDIs, a bone plate 915 is secured to the facial skeleton via screws inserted into through apertures 918 of the contoured portion of the bone plate 915. A post 905 is coupled to a planar portion of the bone plate 915 and extends through the depth of the vertical slot osteotomy 927 in the alveolar ridge 925. From the lateral perspective, the relative dimensions and position of the contoured portion of the bone plate 915 on the facial skeleton, according to an embodiment, are observable. Further, the relative location of the post 905 within the vertical slot osteotomy 927 is observable, as well as the position of a post base 907 relative to an inferior portion of the alveolar ridge 925.

Figure 10:
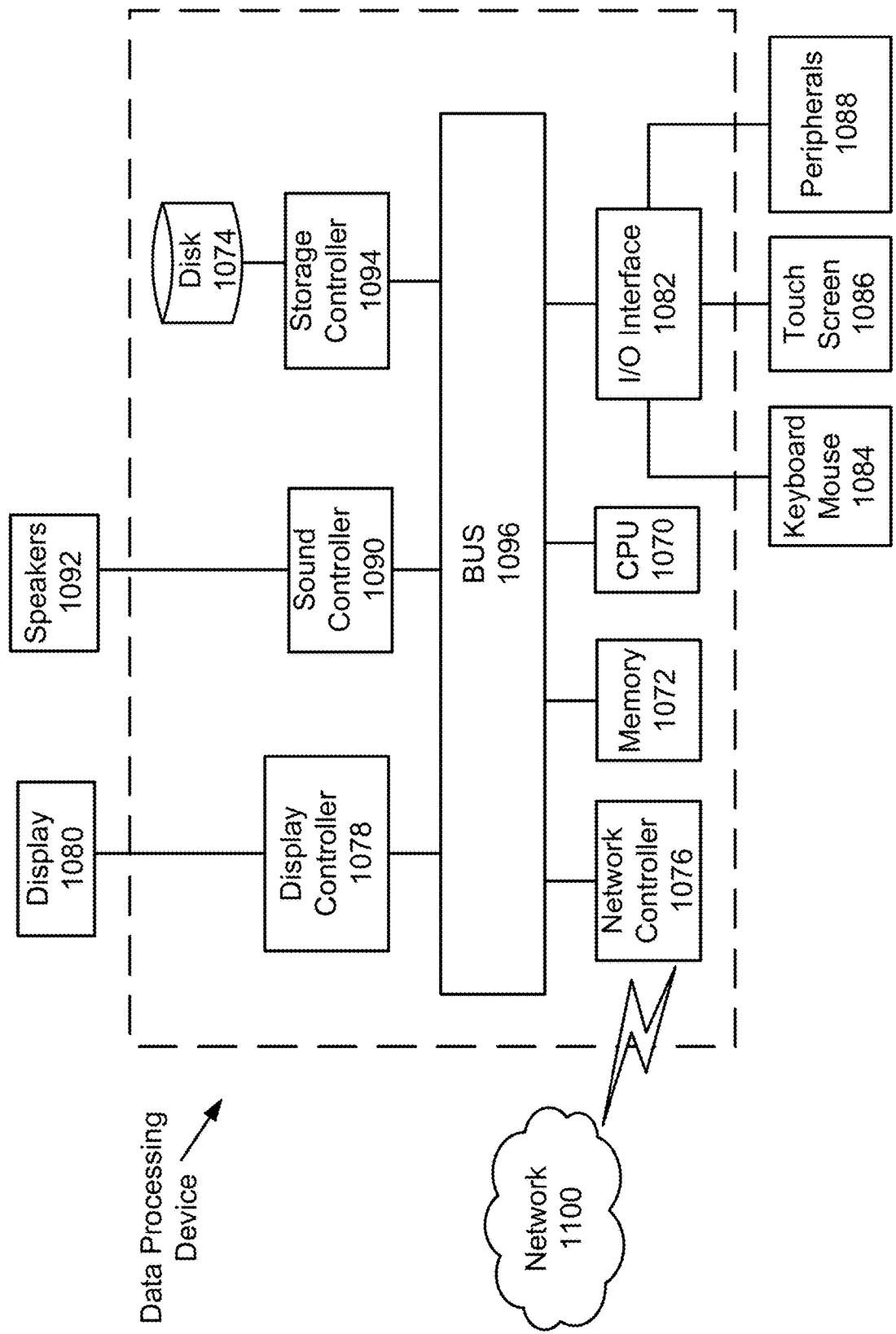
FIG. 10 is a hardware description of a data processing device, according to an exemplary embodiment of the present disclosure.

Next, a hardware description of the data processing device according to exemplary embodiments is described with reference to FIG. 10. In FIG. 10, the data processing device includes a CPU 1070 which performs the processes described above and below. The process data and instructions may be stored in memory 1072. These processes and instructions may also be stored on a storage medium disk 1074 such as a hard drive (HDD) or portable storage medium or may be stored remotely. Further, the claimed advancements are not limited by the form of the computer-readable media on which the instructions of the inventive process are stored. For example, the instructions may be stored on CDs, DVDs, in FLASH memory, RAM, ROM, PROM, EPROM, EEPROM, hard disk or any other information processing device with which the data processing device communicates, such as a server or computer.

Further, the claimed advancements may be provided as a utility application, background daemon, or component of an operating system, or combination thereof, executing in conjunction with CPU 1070 and an operating system such as Microsoft Windows 7, UNIX, Solaris, LINUX, Apple MAC-OS and other systems known to those skilled in the art.

The hardware elements in order to achieve the data processing device may be realized by various circuitry elements, known to those skilled in the art. For example, CPU 1070 may be a Xenon or Core processor from Intel of America or an Opteron processor from AMD of America, or may be other processor types that would be recognized by one of ordinary skill in the art. Alternatively, the CPU 1070 may be implemented on an FPGA, ASIC, PLD or using discrete logic circuits, as one of ordinary skill in the art would recognize. Further, CPU 1070 may be implemented as multiple processors cooperatively working in parallel to perform the instructions of the inventive processes described above.

The data processing device in FIG. 10 also includes a network controller 1076, such as an Intel Ethernet PRO network interface card from Intel Corporation of America, for interfacing with network 1100. As can be appreciated, the network 1100 can be a public network, such as the Internet, or a private network such as an LAN or WAN network, or any combination thereof and can also include PSTN or ISDN sub-networks. The network 1100 can also be wired, such as an Ethernet network, or can be wireless such as a cellular network including EDGE, 3G and 4G wireless cellular systems. The wireless network can also be WiFi, Bluetooth, or any other wireless form of communication that is known.

The data processing device further includes a display controller 1078, such as a NVIDIA GeForce GTX or Quadro graphics adaptor from NVIDIA Corporation of America for interfacing with display 1080, such as a Hewlett Packard HPL2445w LCD monitor. A general purpose I/O interface 1082 interfaces with a keyboard and/or mouse 1084 as well as a touch screen panel 1086 on or separate from display 1080. General purpose I/O interface 1082 also connects to a variety of peripherals 1088 including printers and scanners, such as an OfficeJet or DeskJet from Hewlett Packard.

A sound controller 1090 is also provided in the data processing device, such as Sound Blaster X-Fi Titanium from Creative, to interface with speakers 1092 or microphone thereby providing sounds and/or music.

The general purpose storage controller 1094 connects the storage medium disk 1074 with communication bus 1096, which may be an ISA, EISA, VESA, PCI, or similar, for interconnecting all of the components of the data processing device. A description of the general features and functionality of the display 1080, keyboard and/or mouse 1084, as well as the display controller 1078, storage controller 1094, network controller 1076, sound controller 1090, and general purpose I/O interface 1082 is omitted herein for brevity as these features are known.

In addition to the full arch dental restoration described above, in which immediate loading of the dental prosthesis is possible, situations arise when temporary stabilization of an endosseous dental implant or soft tissue reconstruction is required. In these instances, when it is necessary to transfer occlusal load from endosseous dental implants to skeletal (zygomatic and nasomaxillary) fixation points, the TDI of the present disclosure, with modifications, can be deployed. In an embodiment, the TDI of the present disclosure, with modifications, is a Transvestibular Dental Implant (TVI).

Figure 11:
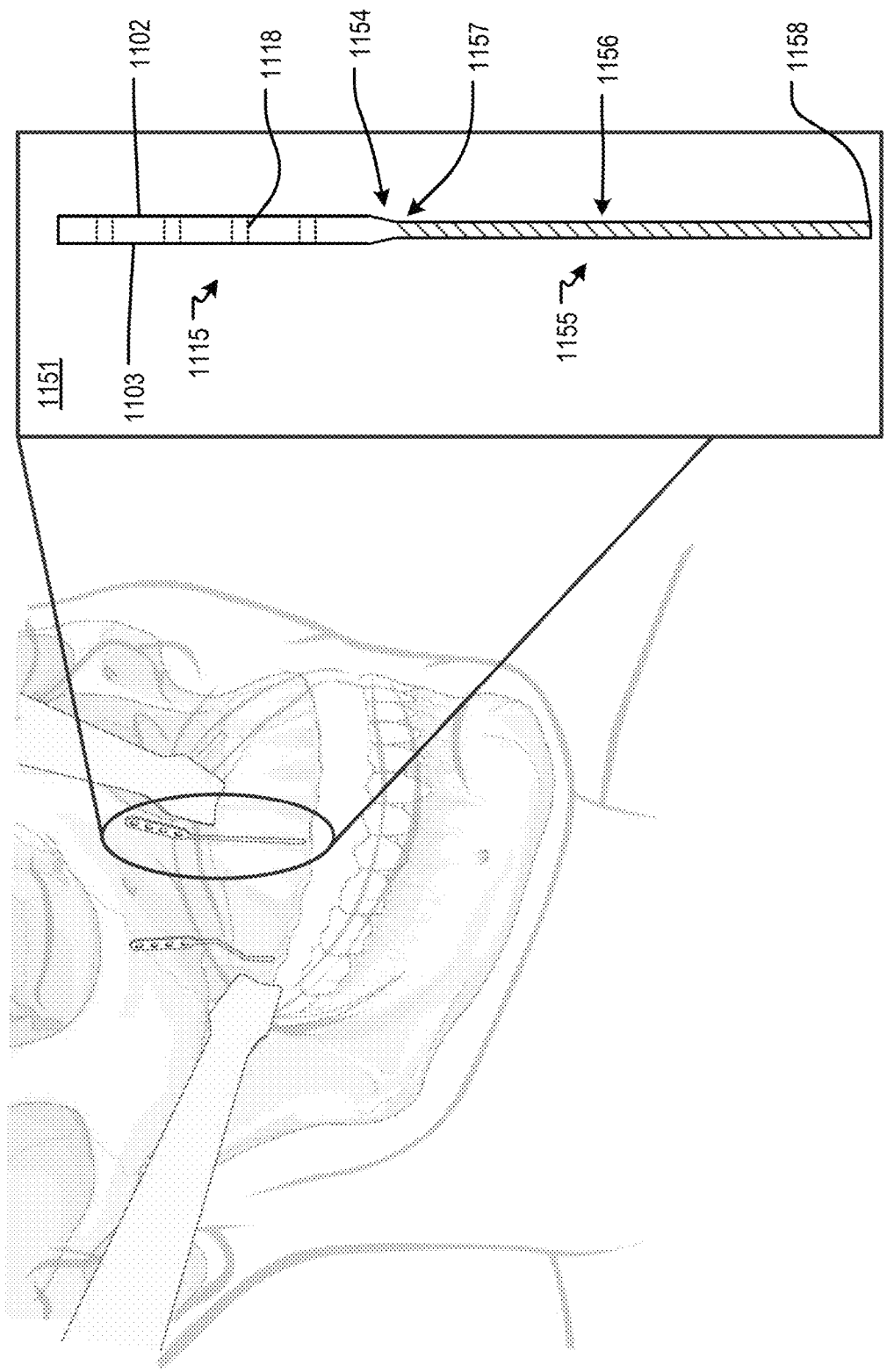
FIG. 11 is a cross-sectional schematic of a transvestibular dental implant, according to an exemplary embodiment of the present disclosure.

FIG. 11 is a cross-sectional schematic of a transvestibular dental implant, according to an exemplary embodiment of the present disclosure. In an embodiment, a transvestibular dental implant (TVI) 1151 is directed to a cortical region of the facial skeleton. The TVI 1151 comprises a bone plate 1115 and a projecting portion 1155. In an example, the projecting portion 1155 is a support rod 1156 of a length for coupling with a dental prosthesis. The support rod 1156 includes a support rod base 1157 and a support rod apex 1158. The support rod base 1157 is configured into the shape of the bone plate 1115. The bone plate 1115 is contoured with respect to a selected region of the facial skeleton determined to be of sufficient bone quality for fixation. The support rod apex 1158 may be configured for coupling with the dental prosthesis. In an example, the support rod apex 1158 may be coupled with the dental prosthesis by a variety of techniques including but not limited to adhesives, resins, or mechanical couplings.

According to an embodiment, the cross-sectional shape of the projecting portion 1155 is circular, as described by the support rod 1156 of the present disclosure. Alternatively, the cross-sectional shape of the projecting portion 1155 of the support rod 1156 may be one selected from a polygonal group including but not limited to triangles, rectangles, pentagons, and hexagons. In an embodiment, a cross-sectional dimension of the support rod 1156 is determined according to a required structural or mechanical sufficiency.

A length of the support rod 1156 is determined according to local cortical bone sufficiency and an axial position of the prosthesis. In an exemplary embodiment, the support rod 1156 has a circular cross-sectional shape with a diameter between 1.50 mm and 2.50 mm and a length between 15 mm and 40 mm.

According to an embodiment, a plurality of through apertures 1118, lacking threads and sized in accordance with appropriate screws, are disposed along the length of the bone plate 1115, passing from an anterior surface 1102 to a posterior surface 1103, for fixation of the TVI 1151, via the posterior surface 1103, to the facial skeleton. In another embodiment, the plurality of through apertures 1118 may be threaded, sized in accordance with appropriate screws, and disposed along the length of the bone plate 1115, passing from the anterior surface 1102 to the posterior surface 1103, for fixation of the TVI 1151, via the posterior surface 1103, to the facial skeleton.

The quality of bone required for fixation of the bone plate 1115 is related, in part, to the selected screws for fixation and relative to a pre-determined minimum cortical bone thickness. In an example, the pre-determined minimum cortical bone thickness is 1.5 mm. In another example, the pre-determined minimum cortical bone thickness is based upon properties of the selected screw, including but not limited to diameter, pitch, and screw length.

As briefly described, the bone plate 1115 of the TVI 1151 is designed in the context of an individual patient's skeletal structure. Following the acquisition and reconstruction of medical images, via data processing device, reflecting the macro- and micro-structure of the bone of the facial skeleton, via techniques including but not limited micro-computed tomography, cone beam computed tomography, and high-resolution magnetic resolution imaging, one or more regions of the facial skeleton are selected as receptive to fixation of a bone plate. According to an embodiment, and as mentioned above, this determination is made based upon local cortical bone thickness, wherein sufficient cortical bone, the dense outer surface of bone, is required to prevent fracture during bone plate fixation. Following region selection, a reconstructed model of the one or more regions of interest is then further manipulated via software (e.g. Mimics, SolidWorks) and prepared for manufacturing, as would be understood by one of ordinary skill in the art. According to an embodiment, the posterior surface 1103 of the bone plate 1115 is contoured relative to the selected facial skeleton region and the anterior surface 1102 of the bone plate 1115 is substantially planar. It should be appreciated that the anterior surface 1102 of the bone plate 1115 may be of a variety of contours, in a nonlimiting manner, such that rigid fixation, via screws through the plurality of through apertures 1118, may be realized.

According to an embodiment, the longitudinal shape of the projecting portion 1155 of the TVI 1151 can be straight, reflecting the post described in FIG. 2 of the present disclosure, or angled in order to approximately follow the contours of the facial skeleton. In another embodiment, and in a manner similar to the above-described bone plate 1115, the projecting portion 1155 of the TVI 1151 can be designed in the context of an individual patient's skeletal structure. Generally, the dimensions of the projecting portion 1155 of the TVI 1151 are pre-determined in order to maximize mechanical properties and minimize aesthetic disorder. The customized approach described herein, specifically, allows for patient-specific design of the projecting portion 1155 of the TVI 1151, thus preserving facial aesthetics while delivering improved prosthesis stabilization. In an example, the patient-specific design of the projecting portion 115, in the context of facial aesthetics, maintains a clearance between the facial skeleton and a dental prosthesis ranging from 1.00 mm to 2.00 mm.

Each bone plate 1115 is manufactured in order to allow for rigid fixation to the facial skeleton of the patient. To this end, and according to an embodiment, the TVI 1151 of the present disclosure can be manufactured from one of a group of materials including but not limited to titanium, cobalt-chrome, cobalt-chrome-molybdenum, cobalt-chrome-nickel, cobalt-nickel-chrome-molybdenum-titanium, calcium phosphate-derivative coated metals, zirconia, zirconium-coated metals, titanium-coated metals, and other biocompatible metals. According to another embodiment, the TVI 1151 of the present disclosure can be manufactured from a material having mechanical properties allowing for bending such that a user may modify the structure as needed in situ, in order to match the contour of the facial skeleton. In an example, the material selected for each component of the TVI 1151 is similar. Further, and according to an embodiment, the TVI 1151 of the present disclosure can be manufactured via a variety of additive manufacturing or subtractive manufacturing techniques including but not limited to direct metal laser sintering, injection molding, iterative plate bending and computer-aided manufacturing. In an example, the TVI 1151 is manufactured from a single anodized titanium rod, wherein the bone plate 1115 is a stamped or milled aspect of the titanium rod. In another embodiment, the bone plate 1115 and the support rod 1156 are manufactured separately, the bone plate 1115 being fabricated according to the above-described techniques and the support rod 1156 being manufactured according to techniques understood by one of ordinary skill in the art. In addition to the TVI 1151 described above, an analogue template TVI 1151 may be similarly manufactured. Following fabrication, the two components of the TVI 1151 can be coupled at a neck 1154 joining an end of the bone plate 1115 with the support rod base 1157. The coupling can be formed by a variety of approaches including but not limited to welding, frictional coupling, and structural adhesives. In the context of the present disclosure, screws are selected for the plurality of through apertures 1118, or may be fabricated according to pre-determined specifications, in order to ensure rigid fixation of the bone plate 1115 to the facial skeleton.

Further, and according to an embodiment, the TVI 1151 of the present disclosure is manufactured according to physical dimensions of the selected skeletal features of each patient. As described above, the bone plate 1115 and projecting portion 1155 of the TVI 1151 can be manufactured according to the selected skeletal region of each patient, the dimensions of the posterior portion 1103 of the bone plate 1115 and the projecting portion 1155 dependent, thereof. The number of through apertures 1118 of the bone plate 1115, likewise, is dependent on the selected skeletal region and the minimum number of screws required to securely fix the bone plate 1115 to the facial skeleton. In an embodiment, and as alluded to above, the support rod 1156 and the anterior portion 1102 of the bone plate 1115 can be selected from a group of pre-determined sizes, their dimensions determined therein. In another embodiment, the support rod 1156 and the anterior portion 1102 of the bone plate 1115 may be custom manufactured according to the needs of the patient, the dimensions of the anterior portion 1102 of the bone plate 1115 and the support rod 1156 being dependent, thereof. It should be appreciated that, using the above-described techniques and approaches, the present disclosure affords the flexibility to fabricate the TVI 1151 with dimensions based upon the needs of the individual patient.

According to an embodiment, a width of the bone plate 1115 is determined according to a selected screw size. A length of the bone plate 1115 is determined according to local cortical bone sufficiency. A thickness of the bone plate 1115 is determined according to the length of the bone plate 1115. In an exemplary embodiment, the bone plate 1115 has a width between 3.00 mm and 5.00 mm, a thickness between 1.50 mm and 3.50 mm, and a length between 6.00 mm and 12.00 mm, depending on cortical bone sufficiency.

Based on dental location, local cortical bone sufficiency, and the stability of other endosseous dental implants supporting an anticipated occlusal load, more than one TVI may be required for dental prosthesis stabilization. In an embodiment, four to six TVIs are positioned across the dental arch in order to support a full arch dental prosthesis. In an example when six TVIs are employed, a centrally located TVI on either side of the dental arch can be diagonally oriented to improve stability.

The manufacturing approach of a TVI, according to an exemplary embodiment, is substantially similar to the approach described previously for a TDI in the flowchart of FIG. 5 of the present disclosure, mutatis mutandis.

FIG. 12A and FIG. 12B are schematics of an anterior view and a perspective view of a TVI, respectively. In an embodiment, and as shown in FIG. 12A, a length 1236 of a bone plate 1215 may be between 15 mm and 40 mm. In another embodiment, the length 1236 of the bone plate 1215 may be between 15 mm and 25 mm. In an example, the length 1236 of the bone plate 1215 may be 20 mm. Further, a length of a contoured portion 1237 of the bone plate 1215 may be between 10 mm and 15 mm according to dimensions of selected skeletal features of the patient. In an example, the length of the contoured portion 1237 of the bone plate 1215 may be 12 mm. Moreover, a width of the contoured portion 1239 of the bone plate 1215 may be between 3.00 mm and 5.00 mm according to dimensions of the selected skeletal features of the patient. In an example, the width of the contoured portion of the bone plate 1239 may be 4.00 mm. As a result, a diameter of a plurality of through apertures 1218 of the contoured portion of the bone plate 1215 may be between 1.75 mm and 2.00 mm. In an example, a diameter of each of the plurality of through apertures 1218 of the contoured portion of the bone plate 1215 may be 1.85 mm. As shown in FIG. 12B, the bone plate 1215 may be further defined according to the thickness of each component. In an embodiment, a thickness of the support rod 1268 or, for instance, a diameter of the support rod 1268, may be between 2.00 mm and 2.50 mm. In an example, the thickness of the support rod 1268 may be 2.25 mm. In another embodiment, a thickness of the contoured portion of the bone plate 1238 may be between 1.50 mm and 3.50 mm. In an example, the thickness of the contoured portion of the bone plate 1238 may be 2.50 mm.

According to an embodiment, the above-described dimensions of the contoured portion of the bone plate 415 may be varied according to the selected skeletal features of the patient. Moreover, the above-described dimensions of the contoured portion of the bone plate 415 may vary locally, the bone plate having been contoured to the local features of the facial skeleton of a patient.

Figure 13:
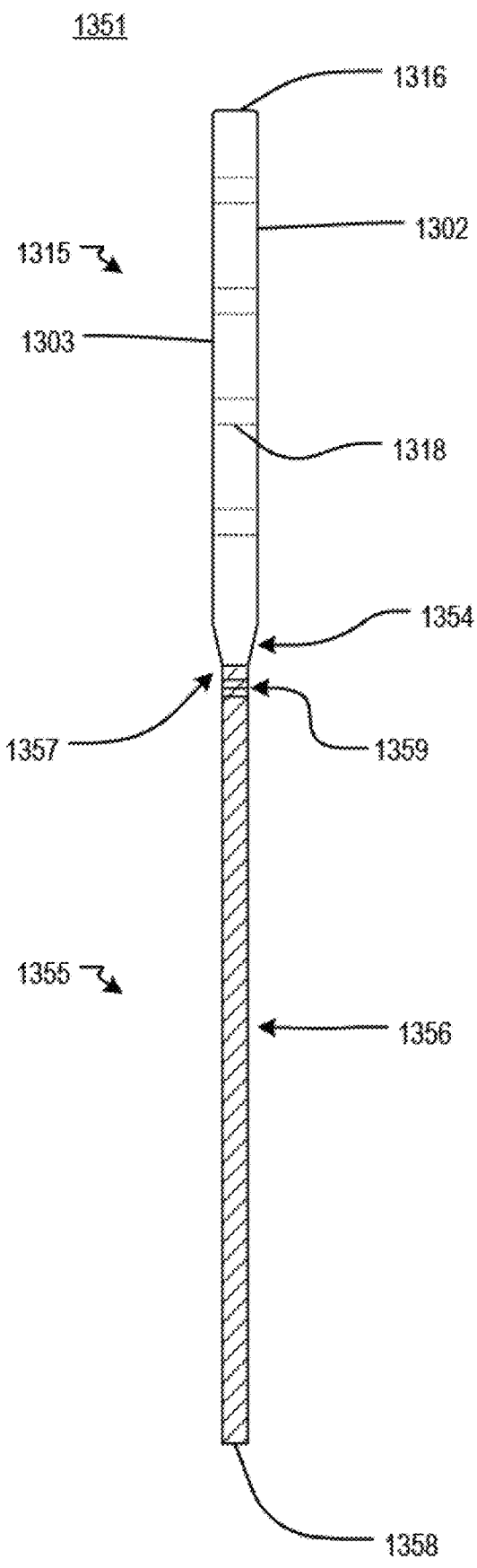
FIG. 13 is a cross-sectional schematic of a transvestibular dental implant, according to an exemplary embodiment of the present disclosure.

FIG. 13 is a cross-sectional schematic of a transvestibular dental implant, according to an exemplary embodiment of the present disclosure. In an embodiment, as described in FIG. 11, a TVI 1351 comprises a bone plate 1315 and a projecting portion 1355. In an example, the projecting portion 1355 is a support rod 1356 of a length for coupling with a dental prosthesis. The support rod 1356 includes a support rod base 1357 and a support rod apex 1358. The support rod base 1357 is configured for coupling with an end of the bone plate 1315. The bone plate 1315 is contoured with respect to a selected region of the facial skeleton determined to be of sufficient bone quality for fixation. The support rod apex 1358 is configured for coupling with the dental prosthesis. In an embodiment, a plurality of through apertures 1318, lacking threads and sized in accordance with appropriate screws, are disposed along the length of the bone plate 1315, passing from an anterior surface 1302 to a posterior surface 1303, for fixation of the TVI 1351, via the posterior surface 1303, to the facial skeleton. In another embodiment, the plurality of through apertures 1318 may be threaded, sized in accordance with appropriate screws, and disposed along the length of the bone plate 1315, passing from the anterior surface 1302 to the posterior surface 1303, for fixation of the TVI 1351, via the posterior surface 1303, to the facial skeleton.

The above-described TVI 1351 is intended to be a temporary device that, upon primary implant stabilization, can be removed. In an embodiment, the TVI 1351 can be removed via reverse surgical procedure, wherein the complete hardware of the TVI 1351 is removed. In another embodiment, as described in FIG. 13, the support rod 1356 may further comprise a biasing feature or, for example, a score 1359 proximate to the coupling between the bone plate 1315 and the support rod 1356. The score 1359, upon application of sufficient force, can fracture, or otherwise deform, causing the support rod 1356 to break away from the bone plate 1315 at a neck 1351 of the TVI 1351. While this approach does not completely remove the TVI 1351 hardware from the patient, it obviates the need for additional surgical intervention. In an embodiment, the score 1359 of the TVI can be manipulated by manual force application via forceps. In an example, the score 1359 of the TVI is a lateral score 1359 extending the perimeter of the support rod 1356.

Figure 14:
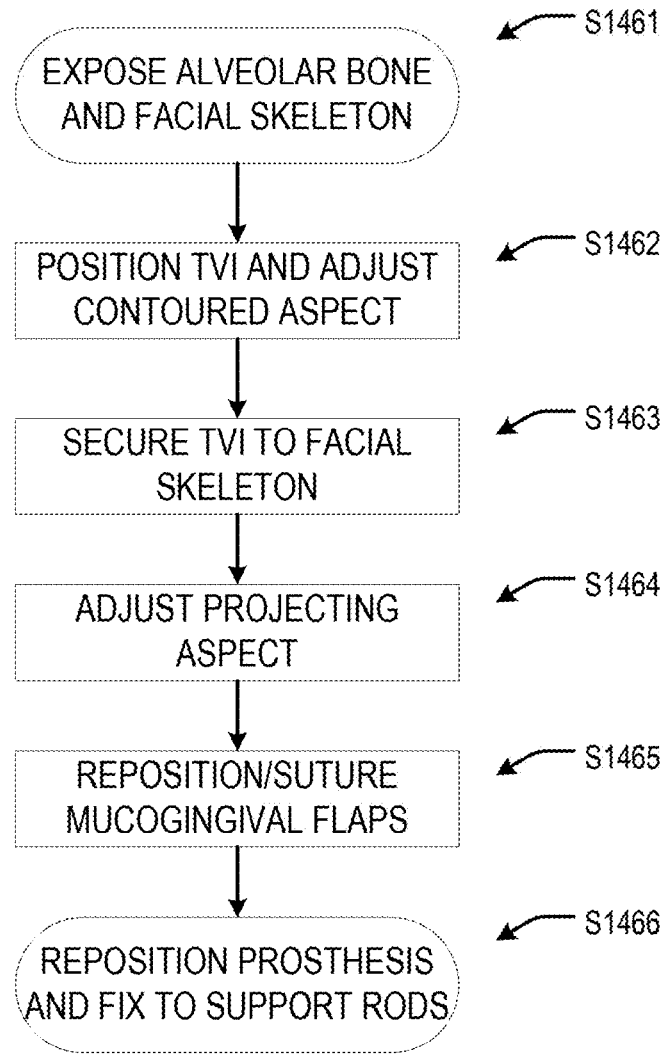
FIG. 14 is a flowchart of implantation of a transvestibular dental implant, according to an exemplary embodiment of the present disclosure.

FIG. 14 is a flowchart of implantation of a transvestibular dental implant, according to an exemplary embodiment of the present disclosure. It should be appreciated that, while FIG. 14 describes implantation of a plurality of TVIs and stabilization of a full dental arch dental prosthesis (e.g. upper or lower), according to an embodiment of the present disclosure, implantation of a single TVI can be performed similarly mutatis mutandis.

In cases of failed endosseous dental implants, it may be possible to retain the original dental prosthesis for use with stabilization methods, such as the TVI of the present disclosure. To this end, implantation of a TVI is substantially similar to the implantation approach of the above-described TDI. Initially, as described in FIG. 14 and according to an embodiment of the present disclosure, the alveolar bone and facial skeleton are exposed following mid-crestal, full arch gingival incisions and reflection of the mucogingival flaps S1461. Following preparation of the facial skeleton, each of four TVIs are positioned proximate to the selected cortical bones of the facial skeleton S1462, wherein the posterior portion of the bone plate is seated. If appropriate, the bone plate can be further shaped in situ in order to properly seat the posterior portion of the bone plate. Upon appropriately seating the TVI to the facial skeleton, the bone plate is fixed to the facial skeleton via a plurality of screws inserted through a corresponding plurality of through apertures of the bone plate S1463. If necessary, and in order to couple the projecting portion apex to the primary dental prosthesis, the projecting portion can then be shaped S1464. Positioning and adjustment of the projecting portion of the TVI can be informed by positioning of the original dental prosthesis. Once adjusted and in a final position, the mucogingival flaps can be repositioned and sutured around the bone plate and projecting portion of the TVI such that only a length of projecting portion necessary for dental prosthesis coupling is observable in the oral cavity S1465. Once the mucogingival flaps have been sutured and the oral environment restored, the original dental prosthesis may be fixed to the TVIs via methods previously described.

Figure 15:
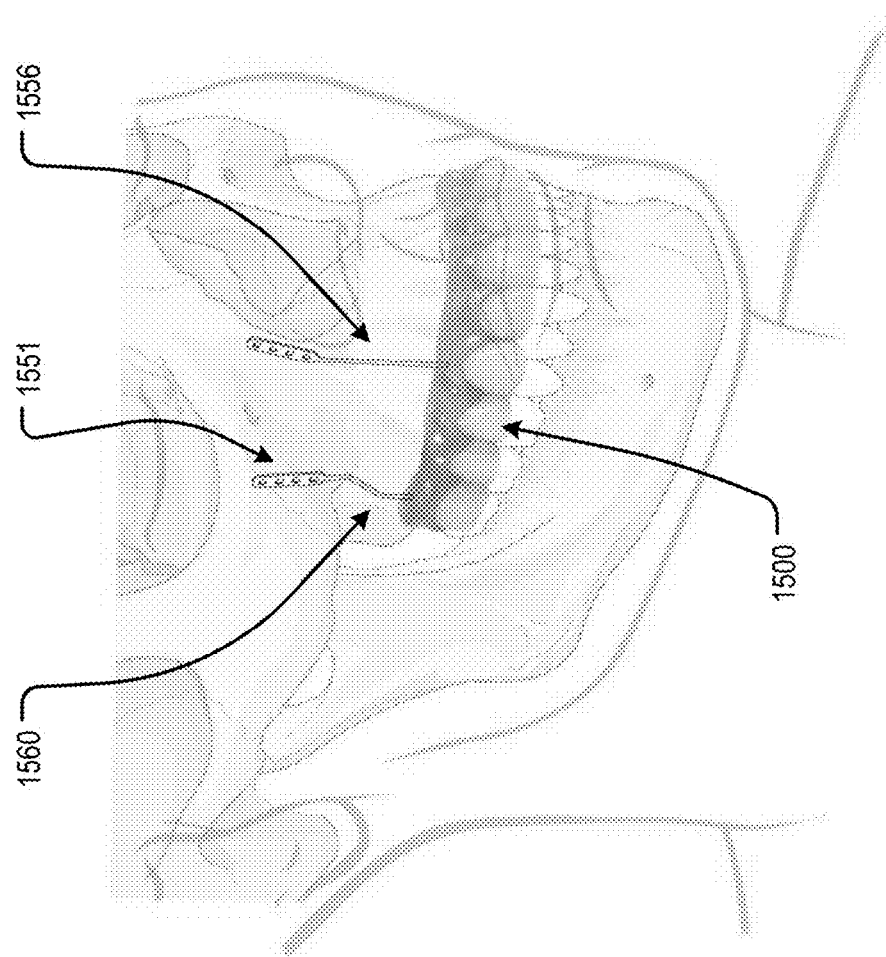
FIG. 15 is an illustration of one or more implanted transvestibular dental implants, according to an exemplary embodiment of the present disclosure.

FIG. 15 is an illustration of one or more implanted transvestibular dental implants, according to an exemplary embodiment of the present disclosure. For each of the one or more implanted TVI 1551, a bone plate is secured to the facial skeleton via screws inserted into through apertures of the bone plate. A support rod 1556 is coupled to an end of the bone plate and extends through from the facial skeleton to a dental prosthesis 1500. From the described perspective, the relative dimensions and position of the bone plate on the facial skeleton, according to an embodiment, are observable. Further, the configuration of the support rod 1556 is observable, as well as an adjusted support rod 1560, angled in order to follow the contours of the facial skeleton. FIG. 15 is an illustration of two TVIs 1551 of a portion of a dental arch, but it should be appreciated that a similar fixation strategy can be applied to the remainder of the dental arch, as appropriate.

Embodiments of the present disclosure may also be as set forth in the following parentheticals.

(1) A dental implant, comprising a bone plate having a planar portion and a contoured portion, and a post, wherein the planar portion of the bone plate and the post are positioned within a vertical slot osteotomy, wherein one or more surfaces of the contoured portion of the bone plate is contoured relative to a selected surface of a bone of a facial skeleton, and wherein the bone plate is configured to be coupled to the facial skeleton.

(2) The dental implant according to (1), wherein the bone plate is fabricated from titanium.

(3) The dental implant according to either (1) or (2), wherein the contoured portion of the bone plate is configured to be coupled to the facial skeleton.

(4) The dental implant according to any of (1) to (3), wherein the selected surface of the bone of the facial skeleton is selected based upon a determination of cortical bone thickness.

(5) The dental implant according to any of (1) to (4), wherein the bone plate further comprises a plurality of through apertures for fixing the dental implant to the facial skeleton.

(6) The dental implant according to any of (1) to (5), wherein a post apex of the post is coupled perpendicularly to a surface of the planar portion of the bone plate within the vertical slot osteotomy.

(7) The dental implant according to any of (1) to (6), wherein the vertical slot osteotomy is performed within the alveolar bone.

(8) The dental implant according to any of (1) to (7), wherein a lateral angle of the bone plate, defined as an angle between a longitudinal axis of the bone plate and an axis of the contoured portion of the bone plate in a first plane, is between −60° and +60°.

(9) The dental implant according to any of (1) to (8), wherein an anterior angle of the bone plate, defined as an angle between a longitudinal axis of the bone plate and an axis of the contoured portion of the bone plate in a second plane, is between −60° and +60°.

(10) The dental implant according to any of (1) to (9), wherein the vertical slot osteotomy is sealed via collagen membrane.

(11) A method of manufacture of a dental implant, comprising acquiring, via processing circuitry, structural data corresponding to a facial skeleton, selecting, via the processing circuitry, a surface of a bone of the facial skeleton based upon a determination of cortical bone thickness, generating, via the processing circuitry, a contoured surface based upon the selection of the surface of the bone of the facial skeleton, and fabricating, based upon an instruction transmitted via the processing circuitry, a bone plate based upon the generated contoured surface, wherein the bone plate comprises a planar portion and a contoured portion, the planar portion of the bone plate being positioned within a vertical slot osteotomy and the contoured portion being positioned proximately to the selected surface of the bone of the facial skeleton, and wherein the bone plate is configured to be coupled to the facial skeleton.

(12) The method of manufacture according to (11), wherein the bone plate is fabricated via direct metal laser sintering.

(13) The method of manufacture according to either (11) or (12), wherein the vertical slot osteotomy is performed via one or more templates based upon the selected surface of the bone of the facial skeleton.

(14) A dental implant, comprising a bone plate having one or more surfaces contoured relative to a selected surface of a bone of a facial skeleton, and a projecting portion, the projecting portion of the dental implant extending from and below the bone plate, wherein the projecting portion is configured to be coupled to a dental prosthesis, and wherein the bone plate is configured to be coupled to the facial skeleton.

(15) The dental implant according to (14), wherein the dental implant is fabricated from titanium.

(16) The dental implant according to either (14) or (15), wherein the bone plate of the dental implant is configured to be coupled to the facial skeleton.

(17) The dental implant according to any of (14) to (16), wherein the selected surface of the bone of the facial skeleton is selected based upon a determination of cortical bone thickness.

(18) The dental implant according to any of (14) to (17), wherein the bone plate of the dental implant further comprises a plurality of through apertures for fixing the dental implant to the facial skeleton.

(19) The dental implant according to any of (14) to (18), wherein the projecting aspect further comprises a biasing feature proximate to the coupling between the projecting portion of the dental implant and the bone plate.

(20) The dental implant according to any of (14) to (19), wherein the biasing feature is configured to fracture in response to a force applied to the projecting portion of the dental implant.

Obviously, numerous modifications and variations are possible in light of the above teachings. It is therefore to be understood that within the scope of the appended claims, the invention may be practiced otherwise than as specifically described herein.

Thus, the foregoing discussion discloses and describes merely exemplary embodiments of the present invention. As will be understood by those skilled in the art, the present invention may be embodied in other specific forms without departing from the spirit or essential characteristics thereof. Accordingly, the disclosure of the present invention is intended to be illustrative, but not limiting of the scope of the invention, as well as other claims. The disclosure, including any readily discernible variants of the teachings herein, defines, in part, the scope of the foregoing claim terminology such that no inventive subject matter is dedicated to the public.

The invention claimed is:

1. A dental implant, comprising:
    a bone plate having a planar portion and a contoured portion, the planar portion and the contoured portion defining opposite ends of the bone plate; and
    a post, wherein
    one or more surfaces of the contoured portion of the bone plate are contoured relative to a selected outer surface of a bone of a facial skeleton, and the contoured portion of the bone plate is configured to be coupled to the selected outer surface of the bone of the facial skeleton,
    the post is coupled perpendicularly, via an apex of the post, to the planar portion of the bone plate, and
    the planar portion and the post are configured to be received inside a vertical slot recess formed in alveolar bone with the post being disposed in the vertical slot recess.

2. The dental implant according to claim 1, wherein the bone plate is fabricated from titanium.

3. The dental implant according to claim 1, wherein the selected outer surface of the bone of the facial skeleton is selected based upon a determination of cortical bone thickness.

4. The dental implant according to claim 1, wherein the bone plate includes a plurality of through apertures for fixing the dental implant to the facial skeleton.

5. The dental implant according to claim 1, further comprising a collagen membrane encapsulating at least a portion of the post of the dental implant.

6. The dental implant according to claim 1, wherein a lateral angle of the bone plate, defined as an angle between a longitudinal axis of the bone plate and an axis of the contoured portion of the bone plate in a first plane, is between −60° and +60°.

7. The dental implant according to claim 1, wherein an anterior angle of the bone plate, defined as an angle between a longitudinal axis of the bone plate and an axis of the contoured portion of the bone plate in a second plane, is between −60° and +60°.

8. The dental implant according to claim 1, wherein
    the bone plate includes one length of the contoured portion connected to the planar portion, and
    the planar portion includes the post coupled thereto.

\* \* \* \* \*